(12) United States Patent
Pena et al.

(10) Patent No.: US 12,702,749 B2
(45) Date of Patent: Aug. 11, 2026

(54) PAD FOR ADHERING A MEDICAMENT DELIVERY DEVICE TO THE SKIN, INCLUDING A NEEDLE

(71) Applicant: SHL MEDICAL AG, Zug (CH)

(72) Inventors: Marcel Pena, Hialeah, FL (US); Hsueh-Yi Chen, New Taipei City (TW); Slobodan Stefanov, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 1004 days.

(21) Appl. No.: 17/911,017

(22) PCT Filed: Mar. 24, 2021

(86) PCT No.: PCT/EP2021/057585
§ 371 (c)(1),
(2) Date: Sep. 12, 2022

(87) PCT Pub. No.: WO2021/209234
PCT Pub. Date: Oct. 21, 2021

(65) Prior Publication Data

US 2023/0119615 A1 Apr. 20, 2023

Related U.S. Application Data

(60) Provisional application No. 63/142,111, filed on Jan. 27, 2021, provisional application No. 63/009,508, filed on Apr. 14, 2020.

(30) Foreign Application Priority Data

May 22, 2020 (EP) .................................... 20176050

(51) Int. Cl.
*A61M 5/142* (2006.01)
*A61M 5/20* (2006.01)

(52) U.S. Cl.
CPC .......... *A61M 5/14248* (2013.01); *A61M 5/20* (2013.01); *A61M 2005/14252* (2013.01)

(58) Field of Classification Search
CPC ................ A61M 5/14248; A61M 5/20; A61M 2005/14252; A61M 5/427; A61M 5/42
See application file for complete search history.

(56) References Cited

U.S. PATENT DOCUMENTS 5,848,990 A * 12/1998 Cirelli .................. A61M 5/158 604/131
7,338,465 B2 3/2008 Patton
(Continued)

FOREIGN PATENT DOCUMENTS

CN 109789268 A 5/2019
EP 2107916 B1 6/2011
(Continued)

OTHER PUBLICATIONS

International Search Report and Written Opinion for Int. App. No. PCT/EP2021/057585, mailed Apr. 28, 2021.

*Primary Examiner* — James D Ponton
(74) *Attorney, Agent, or Firm* — McDonnell Boehnen Hulbert & Berghoff LLP

(57) ABSTRACT

Pads for attaching medicament delivery devices such as autoinjectors to an injection site are presented that include a pad extending along an axis from a proximal end to a distal end, where the proximal end is the end of the pad adjacent to an injection site when the pad is in use, the pad can have an attachment portion configured to receive a medicament delivery device and a second attachment portion attached to the attachment portion, wherein the second attachment portion is arranged at the proximal end of the pad, and wherein the second attachment portion is configured to attach the pad to said injection site when the pad is in use.

15 Claims, 25 Drawing Sheets

(56) References Cited

U.S. PATENT DOCUMENTS

| | | | |
|---|---|---|---|
| 7,985,199 B2 | 7/2011 | Kornerup et al. | |
| 7,993,306 B2 | 8/2011 | Marrs et al. | |
| 8,292,891 B2 | 10/2012 | Browne et al. | |
| 8,469,929 B2 | 6/2013 | Hunn et al. | |
| 8,551,047 B2 | 10/2013 | Burns et al. | |
| 8,945,057 B2 | 2/2015 | Gyrn et al. | |
| 2008/0319416 A1* | 12/2008 | Yodfat | A61M 5/422 604/513 |
| 2010/0298830 A1 | 11/2010 | Browne et al. | |
| 2012/0150115 A1* | 6/2012 | Kamen | F04B 7/00 141/10 |
| 2014/0324021 A1* | 10/2014 | Ulrich | A61K 9/0097 604/116 |
| 2020/0016333 A1 | 1/2020 | Soares et al. | |
| 2021/0308370 A1* | 10/2021 | Arnold | A61M 5/14248 |

FOREIGN PATENT DOCUMENTS

| | | | |
|---|---|---|---|
| EP | 2776115 | B1 | 3/2019 |
| EP | 2836254 | B1 | 6/2019 |
| JP | 3216566 | B2 | 10/2001 |
| JP | 3223479 | B2 | 10/2001 |
| JP | 2009-525822 | A | 7/2009 |
| JP | 5905968 | B2 | 4/2016 |
| JP | 2016-154599 | A | 9/2016 |
| WO | 2007/095093 | A2 | 8/2007 |
| WO | 2013/070705 | A1 | 5/2013 |
| WO | 2016041871 | A1 | 3/2016 |
| WO | 2014/033898 | A1 | 8/2016 |
| WO | 2019/126268 | A1 | 6/2019 |

* cited by examiner 102
106
141
103
12
108
130
144
141

102
103
132
144
112
12
132
142
146
14

30
124
125
102
106
140
126

108

134
112
102
106
103
14
12
10
100

116
108
112
200
154
152
102
116
154
114

102
108
112
152

PAD FOR ADHERING A MEDICAMENT DELIVERY DEVICE TO THE SKIN, INCLUDING A NEEDLE

CROSS REFERENCE TO RELATED APPLICATIONS

The present application is a U.S. National Phase Application pursuant to 35 U.S.C. § 371 of International Application No. PCT/EP2021/057585 filed Mar. 24, 2021, which claims priority to U.S. Provisional Patent Application No. 63/009,508 filed Apr. 14, 2020; U.S. Provisional Patent Application No. 63/142,111 filed Jan. 27, 2021; and European Patent Application No. 20176050.1 filed May 22, 2020. The entire disclosure contents of these applications are herewith incorporated by reference into the present application.

TECHNICAL FIELD

The present disclosure concerns medicament delivery devices such as autoinjectors, and particularly concerns pads for attaching medicament delivery devices such as autoinjectors to an injection site.

BACKGROUND

A number of medical conditions require injections. These days, a number of different injection devices exist, including various types of pen injectors, autoinjectors and on-body devices. Although many of these devices have enabled major improvements in the management of a number of medical conditions, various limitations do still exist in the current technology. Not least amongst these are the difficulties faced by patients that require frequent injections and by patients that need to inject particularly viscous drugs. In considering these problems, the applicant has appreciated that various developments could be made to help improve the medicament delivery devices on the market today, which are set out in more detail below.

SUMMARY

The present disclosure is defined by the appended claims, to which reference should now be made.

In the present disclosure, when the term "distal direction" is used, this refers to the direction pointing away from the injection or dose delivery site during use of a medicament delivery device such as an autoinjector. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

The same direction terminology has been used to describe other components such as the pad—for example, the proximal end of the pad is the part of the pad closest to the dose delivery site (injection site), and the distal end of the pad is the part of the pad furthest from the dose delivery site. In the Figures, the longitudinal direction is the direction of axis 30, with the corresponding circumferential direction 31 and radial direction 32 relative to the axis 30 also shown. The proximal end and the distal end of medicament delivery devices and/or components is also shown as proximal end 50 and distal end 52.

When the wording 'at the injection site' or 'at the dose delivery site' is used in this application, it generally refers to the point where the medicament delivery device (e.g. a needle) enters the patient, along with the surrounding area, for example the area where the pad is attached.

One aspect of the present disclosure comprises a pad extending along an axis from a proximal end to a distal end. The proximal end is the end of the pad adjacent to an injection site when the pad is in use. The pad comprises an attachment portion configured to receive a medicament delivery device such as an autoinjector and a second attachment portion attached to the attachment portion. The second attachment portion is arranged at the proximal end of the pad, and the second attachment portion is configured to attach the pad to said injection site when the pad is in use. This can allow for an autoinjector that takes a long time to inject (for example more than 15 seconds, more than 30 seconds, or more than 1 minute, such as between 1 and 15 minutes), since the autoinjector can now be hands-free during the injection. For example, the FDA (food and drug administration) in the US sets a maximum allowed time that an autoinjector takes to inject a drug, and a hands-free autoinjector could allow for longer injection times.

In one embodiment, the second attachment portion is an adhesive portion, and the adhesive portion is configured to adhere the pad to said injection site when the pad is in use.

In one embodiment, the attachment portion is at the distal end of the pad. Alternatively, the medicament delivery device could also be attached to the side of the pad (making the longitudinal axis of the medicament delivery device parallel to the surface at the injection site).

In one embodiment, the adhesive portion of the pad comprises a flange, and the flange extends further from the axis in a radial direction than the attachment portion. The flange can provide increased adhesive area and therefore a stronger attachment to the injection site, and/or can provide greater comfort to the user/patient by spreading the pressure of pushing a medicament delivery device towards the injection site, for example to activate an autoinjector. The flange is typically attached to the attachment portion of the pad on one side and the adhesive on the other. In one embodiment, the flange is flexible. This can help attach the pad to the injection site by flexing to follow the shape of the injection site. In one embodiment, the flange extends generally perpendicular or perpendicular to the axis.

In one embodiment, the adhesive portion comprises an adhesive layer. In one embodiment, the adhesive portion comprises an adhesive layer cover that covers the adhesive layer.

In one embodiment, the attachment portion comprises a tubular portion. The tubular portion can be configured to receive a medicament delivery device such as an autoinjector. The tubular portion can help support the medicament delivery device.

In one embodiment, the pad comprises a medicament delivery member. This can provide a number of benefits. For example, it can allow for multiple injections-either one immediately after the other, or alternatively spread out over a period of time, for example hours or days or even weeks. The pad can be left at the same location, for example for up to 3 days or up to 10 days. Since the medicament delivery member is in the pad, it can allow for medicament delivery devices without medicament delivery members, which can reduce needle-stick injuries, for example, particularly in users that have dexterity and/or eyesight problems. It can reduce the number of new injections that are needed, since multiple injections can be carried out through the same medicament delivery member on the pad, and can avoid users having to remember where their last injection site was to avoid reusing the same injection site. It can also make use of the medicament delivery device simpler, and/or the design of the medicament delivery device simpler—for example, there may no longer be any need for a protective and retractable cover or guard on the medicament delivery device to protect against needle stick injuries. By reusing the pad, it can potentially reduce waste. It can make the depth of injection less variable, as the medicament delivery member extends a relatively fixed distance into the injection site (whereas with a syringe or an autoinjector, for example, the user might not fully insert the needle and end up with a painful intradermic injection).

In one embodiment, the medicament delivery member is a cannula, for example a soft or flexible cannula. This can be more comfortable than a rigid solution such as a metal needle. In one embodiment, the pad comprises an insertion mechanism configured to insert the medicament delivery member into the injection site. In one embodiment, the insertion mechanism comprises a needle for inserting the medicament delivery member into the injection site. In one embodiment, the needle of the insertion mechanism and/or the medicament delivery member such as a cannula is offset from the axis. In one embodiment, the attachment portion and the needle of the insertion mechanism are spaced apart in a radial direction relative to the axis. In general, the axis should be considered to extend through the pad at the point where the medicament delivery device would be centred when it is in place in the pad—for example through the centre of the attachment portion of the pad. Spacing apart or offsetting the components in this manner can allow the width of the pad in the axial direction to be reduced compared to solutions where the components are coaxial, which can make it more practical to keep the pad on the skin under clothes—as the attachment portion and the insertion mechanism can then overlap with one another in the axial direction, for example.

In one embodiment, the pad comprises an insertion or medicament container insertion needle configured to pierce a medicament delivery container of a medicament delivery device. In one embodiment, the insertion needle is spaced apart from the needle for inserting the medicament delivery member into the injection site. In one embodiment, the pad comprises a tube extending between the medicament delivery device insertion needle and the medicament delivery member.

In one embodiment, the attachment portion is configured to releasably receive the medicament delivery device or to removably attach an autoinjector to the pad. This allows for the pad and autoinjector to be separated after the injection, for example to dispose of them separately or to allow the autoinjector to be removed without removing the pad (so that the pad can be left for another later injection). This can be particularly useful where a patient suffers from a condition that requires frequent injections (for example daily or multiple times a day), or where a patient suffers from multiple conditions and therefore has several injections that need to be taken one after the other, for example if patients are suffering from multiple autoimmune disorders, diabetes (insulin) and/or growth hormone deficiency.

In one embodiment, the attachment portion comprises a friction lock. In one embodiment, the attachment portion comprises a release mechanism which, upon being actuated, releases the medicament delivery device from the pad. In one embodiment, the release mechanism comprises a button or a slider.

In one embodiment, the attachment portion comprises a slider. In one embodiment, the slider comprises a first arm and a second arm, wherein the first arm and the second arm are spaced apart from one another and configured to grip a medicament delivery device between the first arm and the second arm. In one embodiment, the first arm has a first end and a second end and the second arm has a first end and a second end, wherein the first end of the first arm is attached to the first end of the second arm, and wherein the second end of the first arm and the second end of the second arm are spaced apart from one another. In one embodiment, the arms are joined together only at one end of the arms.

In one embodiment, the first arm and the second arm are flexible so that the second ends of the first arm and the second arm can move relative to one another. In one embodiment, the first arm and the second arm are configured to form a locking position and a release position. In one embodiment, the locking position and the release position each describe an opening between the arms, and wherein the distance between the arms of the opening of the release portion is larger than the distance between the arms of the opening of the locking position. In one embodiment, the openings are circular. In one embodiment, the attachment portion comprises a housing, and the slider is arranged inside the housing.

In one embodiment, the attachment portion comprises a user manipulation portion and a medicament delivery device engagement portion, wherein the attachment portion is configured such that when a user manipulates the user manipulation portion, the medicament delivery device engagement portion can be disengaged from said medicament delivery device.

In one embodiment, the user manipulation portion comprises a flexible section extending around the axis, wherein the attachment portion is configured such that when the user changes the shape of the flexible section (for example by pressing the handles), at least a portion of the medicament delivery device engagement portion is moved further from the axis.

In one embodiment, the flexible section is a flexible elliptical section, and wherein the attachment portion is configured such that changing the shape of the flexible section reduces the ellipticalness of the flexible elliptical section. In one embodiment, the user manipulation portion is attached to the medicament delivery device engagement portion by one or more arms. In one embodiment, the medicament delivery device engagement portion comprises a groove or a protrusion configured to engage with a corresponding protrusion or groove on said medicament delivery device.

In one embodiment, the attachment portion comprises an arm configured to engage a feature of a medicament delivery device. In one embodiment, the arm extends substantially parallel or parallel to the axis. In one embodiment, the arm is configured to engage with a window frame of said medicament delivery device. In one embodiment, the arm comprises a protrusion extending perpendicular to the axis. In one embodiment, the protrusion is configured to engage with a window frame of said medicament delivery device. In one embodiment, the attachment portion comprises a handle and an engagement portion attached to the handle, wherein the engagement portion is configured to releasably attach to an attachment portion of said medicament delivery device such that the engagement portion is released from the medicament delivery device when the handle is pushed towards the axis. In one embodiment, the engagement portion is between the axis and the handle.

In one embodiment, the attachment portion comprises a first handle, a second handle, a first engagement portion and a second engagement portion, wherein the first engagement portion and the second engagement portion are each configured to releasably engage with an attachment portion of said medicament delivery device, wherein the first handle is attached to the first engagement portion and the second handle is attached to the second engagement portion, and wherein pushing the first handle towards the second handle releases the engagement portions from the attachment portion of said medicament delivery device. In one embodiment, the first engagement portion is between the axis and the first handle, and wherein the second engagement portion is between the axis and the second handle. In one embodiment, pushing the handle or handles towards the axis moves at least a part of the engagement portion in the circumferential direction relative to the axis.

In one embodiment, the attachment portion is configured to receive a medicament delivery device with a longitudinal axis of the medicament delivery device extending perpendicular to the axis (30). In one embodiment, the attachment portion comprises a tubular portion, and wherein a longitudinal axis of the tubular portion extends perpendicular to the axis (30). In one embodiment, the pad comprises a medicament delivery member and the attachment portion comprises a button, and wherein pressing the button moves the medicament delivery member in the proximal direction. In one embodiment, the pad comprises a resilient member and a housing, and the resilient member extends between the housing and the button. In one embodiment, the pad comprises a housing, wherein the pad comprises a medicament delivery member housing comprising a cannula, and wherein the medicament delivery member housing is arranged in the housing. In one embodiment, the medicament delivery member housing comprises a channel and the channel is not aligned with the attachment portion before the button is pressed and the channel is aligned with the attachment portion after the button is pressed. In one embodiment, the pad is arranged so that a medicament delivery can only occur after the button has been pressed. In one embodiment, the pad comprises a gas canister and a plunger rod configured to engage a cartridge, wherein activation of the gas canister results in the plunger rod causing expulsion of a medicament from said cartridge.

In another aspect of the present disclosure, a medicament delivery member guard is provided that comprises a pad as described above. In another aspect of the present disclosure, a medicament delivery device is provided that comprises the medicament delivery member guard. In another aspect, apparatus is provided that comprises a pad as described above and a medicament delivery device. In one embodiment, the medicament delivery device comprises a guard. In one embodiment, the guard is a medicament delivery member guard or a membrane guard. In one embodiment, the medicament delivery device comprises a protrusion or recess configured to engage with the attachment portion of the pad. In one embodiment, the medicament delivery device comprises a housing, and wherein the protrusion or recess is on the housing. In one embodiment, the medicament delivery device comprises a window frame, and the attachment portion of the pad is configured to engage the window frame.

In one embodiment, the medicament delivery device is an autoinjector. In one embodiment, the medicament delivery device comprises a medicament container. In one embodiment, the medicament delivery device comprises a medicament delivery member In another aspect of the present disclosure, an autoinjector is provided comprising a housing, wherein the housing comprises an attachment portion, wherein the attachment portion is configured to engage with a corresponding attachment portion on a pad as described above.

Another aspect of the present disclosure concerns a method of carrying out an injection, the method comprising the steps of attaching a pad to an injection site, attaching an autoinjector to the pad and removing the autoinjector from the injection site. In one embodiment, the method additionally comprises the step of removing the pad from the injection site. In one embodiment, the injection automatically starts when the autoinjector is attached to the pad. In one embodiment, the autoinjector and the pad are removed together from the injection site. In one embodiment, the autoinjector is removed from the pad, and the pad is subsequently removed from the injection site.

Another aspect of the present disclosure concerns a method of carrying out an injection, the method comprising the steps of attaching a pad to a dose delivery site, attaching a medicament delivery device to the pad, injecting a medicament into the dose delivery site, and removing the medicament delivery device. In one embodiment, the step of attaching a pad to a dose delivery site consists of attaching the pad and inserting a medicament delivery member into the dose delivery site. In one embodiment, the pad is a pad as described above.

Another aspect of the present disclosure concerns a pad configured to attach a medicament delivery device to a medicament delivery site to carry out an injection, the pad comprising an adhesive for attaching the pad at the medicament delivery site and an attachment portion configured to hold a medicament delivery device at the medicament delivery site. In one embodiment, the medicament delivery device is an autoinjector or a medicament cartridge. In one embodiment, the pad is configured to hold the medicament delivery device at the medicament delivery site for the duration of an injection. In one embodiment, the pad is configured to support the medicament delivery device so that the injection can proceed in a hands-free manner once the injection has started.

Another aspect of the present disclosure concerns a pad for attaching an autoinjector to a user, the pad comprising an adhesive portion for attachment to a medicament delivery site and a housing attached to the adhesive portion, the housing comprising an attachment portion, and wherein the attachment portion is for attaching an autoinjector to the pad. In one embodiment, the pad is attached to the autoinjector such that the autoinjector can be used in a hands-free manner.

Another aspect of the present disclosure concerns a method of hands-free injection of a medicament, the method comprising attaching a pad to a dose delivery site, attaching a medicament delivery device to the pad, injecting a medicament into the dose delivery site while the medicament delivery device is attached to the pad, and removing the medicament delivery device.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which:

FIG. 43 shows an exploded perspective view of some of the components of the pad of FIG. 42, with the housing shown as see-through.

DETAILED DESCRIPTION

Figure 2:
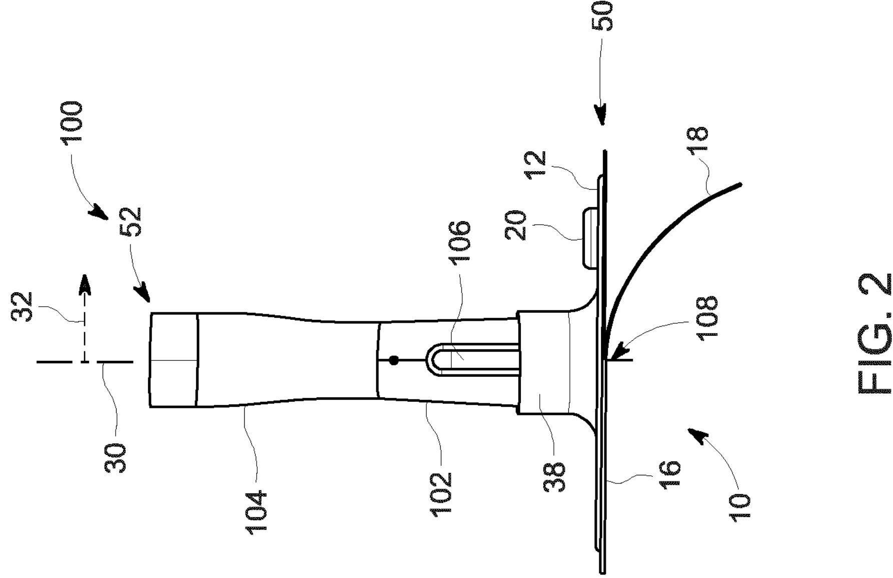
FIG. 2 shows a side view of the pad and autoinjector in FIG. 1.
Figure 1:
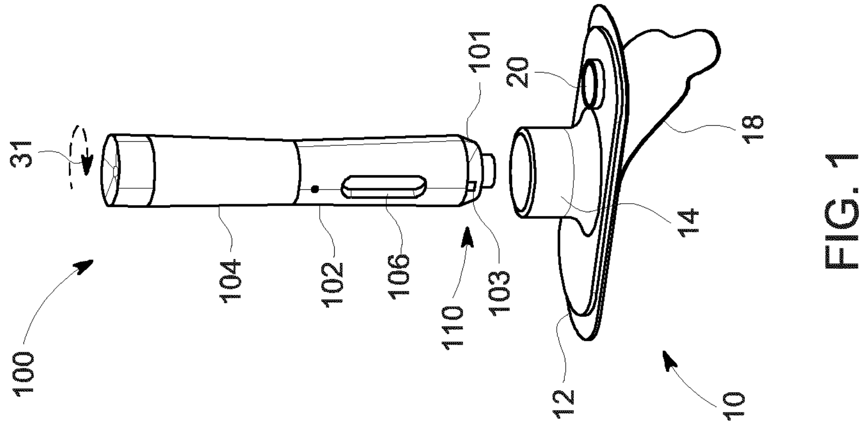
FIG. 1 shows a perspective view of a pad and an autoinjector.

FIGS. 1 and 2 show an example of a pad 10 according to the present disclosure in combination with a corresponding medicament delivery device such as an autoinjector 100. In general, the pad 10 extends along an axis 30 from a proximal end to a distal end, where the proximal end 50 is the end of the pad 10 adjacent to an injection site (drug delivery site) when the pad 10 is in use. The pad 10 comprises an attachment portion 14 configured to receive the autoinjector 100. The pad 10 also comprises a second attachment portion such as an adhesive portion 16 attached to the attachment portion 14, wherein the adhesive portion 16 is arranged at the proximal end 50 of the pad 10, and wherein the adhesive portion 16 is configured to attach the pad 10 to said injection site when the pad 10 is in use.

The adhesive portion 16 comprises an adhesive (not shown), an optional adhesive portion cover 18 and an optional flange 12. The attachment portion 14 comprises an optional release button 20. The attachment portion 14 is designed to receive the corresponding autoinjector 100 to attach the autoinjector 100 to the pad (see FIG. 2). The flange 12 extends away from the attachment portion relative to an axis 30. The adhesive is attached to the flange 12, and an adhesive portion cover 18 is attached to the adhesive portion—in FIGS. 1 and 2, the adhesive portion cover 18 is shown partly removed. The release button 20 is attached to the flange 12 and is configured such that actuating the button releases the autoinjector from the pad. Alternatively, a different shape or type of actuator for the user to interact with could be provided instead of the button 20. For example, the release button can move relative to the pad in the axial direction and/or perpendicular to the axial direction. For example, the release button can be configured to be pushed towards the attachment portion 14, thereby disengaging an engagement member (not shown in FIGS. 1 and 2) in the attachment portion 14 from the attachment portion 110 of the autoinjector 100, to allow the autoinjector to be removed from the pad. Further details of possible features for the attachment portion are described in more detail below and with reference to the Figures.

The autoinjector 100 in FIGS. 1 and 2 extends from a proximal end 50 to a distal end 52 relative to an axis 30. The autoinjector comprises a housing 102, a grip 104, a window 106 and a needle 108. The autoinjector also comprises an attachment portion 110, which is configured to engage with the attachment portion 14 of the pad.

The attachment portion 14 of the pad and the attachment portion 110 of the autoinjector are not shown in detail. Various options are available for the attachment portion, as outlined in further detail in the examples below. To give just a couple of examples, the slider concept from FIG. 3 could be used with the release button in FIG. 1, for example with the button moving parallel to the axis and pushing the slider or with the button directly attached to the slider and moving perpendicular to the axis (i.e. towards and away from the axis). Another option would be a friction lock. A further option would be a snap-fit lock, where a protrusion 103 on the proximal end of the housing 102 of the autoinjector 100 engages with a corresponding part on the attachment portion of the pad, locking the autoinjector into place. The autoinjector could be attached permanently (i.e. not designed to be removed), or could be removably attached. For example, the autoinjector could be removable by simply pulling the autoinjector in the distal direction to disengage the lock, or by twisting the autoinjector in a circumferential direction 31 relative to the axis 30. Twisting the autoinjector could, for example, result in a sloped surface on the proximal end of the autoinjector (extending in the circumferential direction 31 and angled relative to a radial direction 32) engaging with a corresponding portion of the attachment portion 14 of the pad to help disengage the snap-fit lock. Yet another option would be for the autoinjector to first be inserted into the attachment portion 14 of the pad and then twisted in the circumferential direction to lock the autoinjector in place. For removable autoinjectors, the autoinjector could be twisted back after use, for example, to disengage the autoinjector.

An example method of use for the example in FIGS. 1 and 2 will now be described. First, the adhesive portion cover 18 is removed from the pad 10 (in cases where an adhesive portion cover is provided). The pad 10 is then attached at the injection site (dose delivery site) by placing the adhesive portion 16 against the injection site so that the adhesive attaches to the injection site. The autoinjector 100 is then taken and inserted into the attachment portion 14 of the pad. The attachment portion 110 of the autoinjector 100 will then engage the attachment portion 14 of the pad, attaching the autoinjector to the pad and by extension to the injection site.

In an autoinjector where medicament delivery is initiated by simply pushing the autoinjector against the injection site (for example so that the needle shield of the autoinjector is pushed into the device and triggers medicament expulsion), the medicament delivery would typically be triggered at the same time as the attachment portions of the pad and the autoinjector engage with one another. This is an example of a two-step autoinjector (press against injection site, remove from actuation site after injection is complete). In an autoinjector comprising an actuator such as a button (not shown), the medicament delivery would typically not be triggered immediately upon engagement of the attachment portions of the pad and the autoinjector-a further step, namely triggering the actuator, would also be required for the medicament delivery to be triggered. This is an example of a three-step autoinjector (press against injection site, trigger actuator, remove from actuation site after injection is complete). The start of medicament delivery (injection) is typically indicated by a tactile, visual or audible indication such as a click.

Once medicament delivery has been completed (which is typically also indicated by a tactile, visual or audible indication such as a click), the autoinjector can then be disengaged from the pad using the button 20. Once the autoinjector has been disengaged, the pad can also be removed from the injection site, or can be left in place for subsequent injections. Alternatively, if the autoinjector is not removable from the pad, the pad and autoinjector can be removed from the injection site together.

Figure 3:
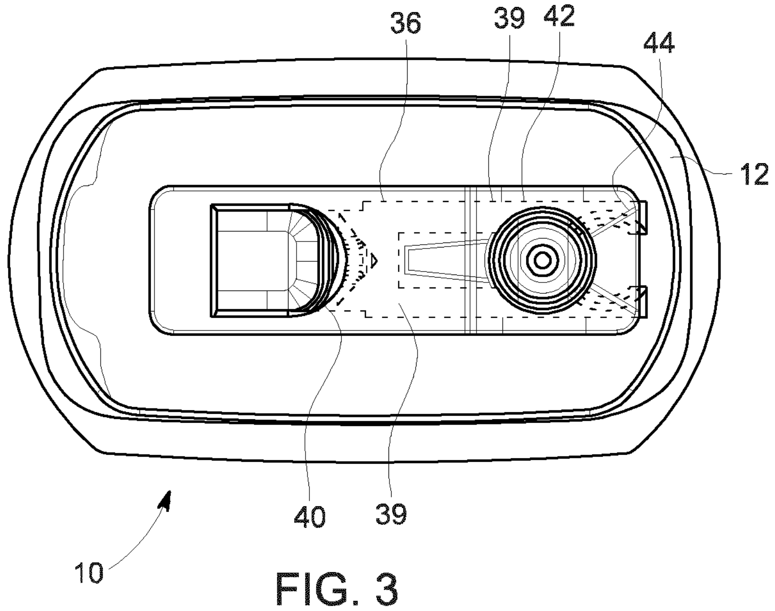
FIG. 3 shows a cross-sectional view in the proximal direction of a pad with part of the pad shown as translucent, along with part of an autoinjector.
Figure 4:
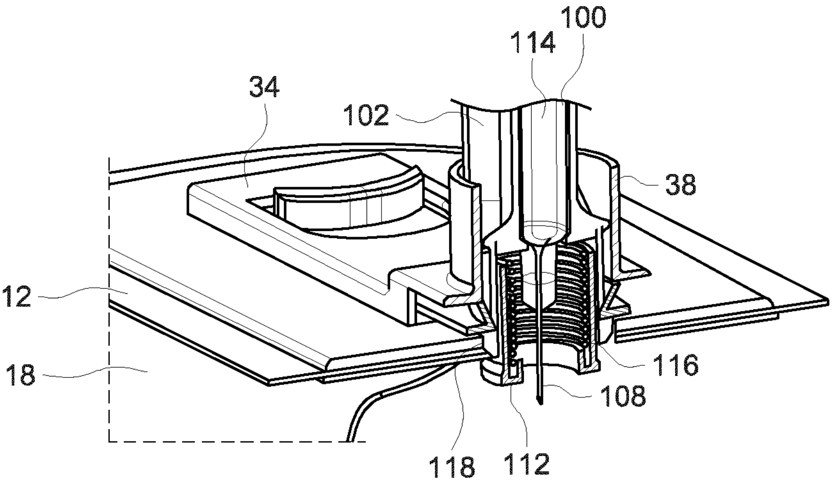
FIG. 4 shows a perspective cross-sectional view of the pad and autoinjector in FIG. 3.

FIGS. 3 and 4 show another example of a pad 10. Initially referring primarily to FIG. 3, the pad 10 comprises a flange 12, an attachment portion comprising a housing 34, a slider 36 and a tubular portion 38, an adhesive (not shown) and an adhesive portion cover 18. The slider 36 comprises a button or handle 40 and two slider arms 39. The arms can be thought of as an autoinjector engagement section of the slider, with the handle being a user engagement section. The arms 39 are both attached to the handle 40, and extend parallel to one another and spaced apart from one another. At the end of the arms distal from the handle, the arms are shaped to form a lock portion 42 and a release portion 44.

Looking now primarily at FIG. 4, further details of the corresponding autoinjector 100 can be seen. In particular, a housing 102, a needle 108, a needle guard 112, a medicament container 114, a needle guard spring 116 and a protrusion or ridge 118 can be seen. The attachment portion of the autoinjector in this case could be considered as comprising the protrusion or ridge 118.

In this particular example, the lock portion 42 partially describes a circle between the arms 39, and the release portion 44 similarly partially describes a circle between the arms 39. In other words, each arm comprises two cut-outs on the side of the arm that faces the other arm, and the cut-outs each describe an arc that is part of a circle—the arcs are typically shaped to correspond to the shape of the corresponding medicament delivery device or devices that the pad is designed to be used with. The full circles of the lock portion and the release portion overlap, though they could also be spaced apart. The circumference of the release portion circle is greater than the circumference of the lock portion circle (the circle defined by one cut-out on the arm has a greater radius than the circle defined by the other cut-out). This allows an appropriately dimensioned autoinjector to pass through the release portion circle but not through the lock portion circle. As a result, when the autoinjector is in the lock portion circle, it is locked in place by the protrusion or ridge 118 on the autoinjector and the lock portion 42 of the slider arms 39. In this example, the circle further from the handle has a greater circumference than the circle closer to the handle (and therefore the handle is closer to the axis in the lock position than in the release position), although the opposite is also possible.

The slider 36 is moveable relative to the housing 34 of the pad. When the slider is moved so that the release portion 44 is aligned with the tubular portion 38, an autoinjector can be inserted into the tubular portion 38. When the lock portion 42 is aligned axially with the tubular portion 38, the autoinjector cannot be inserted into (or can only be inserted a limited distance into) the tubular portion 38. In other words, the autoinjector can only be functionally inserted into the slider housing to carry out an injection when the release portion of the slider is aligned with the tubular portion.

The method of use of the example in FIGS. 3 and 4 will now be described in more detail. As with the example in FIGS. 1 and 2, the optional adhesive portion cover 18 is first removed from the pad. The adhesive portion is then attached to the injection site. Once the pad is in place at the injection site, the slider is placed in a position where the release portion 44 is aligned with the tubular portion 38 (if the slider is not already in that position). The autoinjector 100 is then inserted into the tubular portion 38. Depending on the type of autoinjector, the injection may start as soon as the autoinjector is fully inserted into the tubular portion 38, or it may only start subsequently once an actuator such as a button on the autoinjector is pressed, for example.

Once the autoinjector is fully inserted into the tubular portion, the slider 36 is moved from a position where the release portion 44 is aligned with the tubular portion 38 to a position wherein the lock portion 42 is aligned with the tubular portion 38. This secures (or locks) the autoinjector in the pad, meaning that the user can remove their hands entirely and allow the injection to continue.

The slider does not need to have the particular shape shown in FIGS. 3 and 4, and the shape of the slider arms 39, the button/handle 40, the lock portion 42 and the release portion 44 can be altered. In one alternative, the arms are tapered so that the distance between them reduces the closer you get to the handle—for example, the distance between them constantly reduces the closer you get to the handle. Although in some cases this may be disadvantageous compared to the circles of the example in FIGS. 3 and 4 (for example because it does not necessarily allow for clear-cut lock and release positions, depending on the exact shape), it could allow for a wider range of medicament delivery devices to be used with the same pad (as it does not require a particular diameter or shape of medicament delivery device), which could be useful in terms of practicality and cross compatibility.

In some examples, the slider does not have two arms, and instead has one arm, for example. An example of a pad in which the slider only has one arm is a pad that is designed to function with an autoinjector that has a recess or notch on the side of the autoinjector, for example in the housing (although in general any form of variation of diameter in the axial direction, including protrusions, could also be used). To lock the autoinjector to the pad, the arm is moved into the recess or notch.

The protrusion or ridge 118 in FIG. 4 could either be a protrusion (or plurality of protrusions) extending away from the housing relative to the axis, or it could be one or more ridges extending away from the housing relative to the axis and extending partially or entirely around the circumference of the autoinjector.

Examples of an alternative design will now be provided with reference to FIGS. 3 and 4. As well as the various options for the design of the pad, numerous options are available in terms of amending autoinjector design to allow the pad to influence the operation of the autoinjector. For example, the autoinjector could be designed so that it can only be unlocked for use when engaged correctly with the pad, stopping the autoinjector from being used without the pad. This could be useful to ensure user compliance in cases where use of a pad is necessary (for example for long injections where a pad should be used to provide hands-free injection to comply with FDA regulations), as the injection could not be carried out unless used with the correct pad. An example of such an autoinjector will now be described with reference to the example pad in FIGS. 3 and 4. As already mentioned above, it is relatively common practice to provide an autoinjector in which a button is provided where the user has to press the button to initiate injection, for example by releasing a spring in a powerpack within the autoinjector. The button is typically fairly large and is placed in a position where the user can easily operate it whilst holding the autoinjector, such as on the distal end of the autoinjector or on the side of the autoinjector. In an alternative approach, the button could be made to be difficult to press by the user, for example by reducing the size of the button, by putting the button in a place the user will not typically hold, or by putting the button in a recess in a manner similar to the reset buttons commonly found on electronic devices. To provide a specific example: a button could be provided on the portion of the housing 102 of the autoinjector 100 that is encompassed by the tubular portion 38 of the pad 10 in FIG. 4. The button is in a recess in the housing, making it difficult for a user to push the button (accidentally or deliberately). When the autoinjector is inserted into the pad, the button lines up with one of the arms 39 of the slider 36. When the arms 39 of the slider 36 move from the release position to the lock position, one of the arms is pushed against the button on the autoinjector, releasing the powerpack so that the injection commences (or alternatively simply unlocking the device so that the user can initiate injection by pressing another button elsewhere on the housing). One particular benefit of this example is that it can force compliance with the need to use a pad, not allowing the autoinjector to simply be used without the pad if the user does not follow the use instructions. Different medicament delivery devices could also have differently shaped recesses (or multiple recesses in particular patterns) to stop particular medicament delivery devices from being used on the wrong pad.

Figure 5:
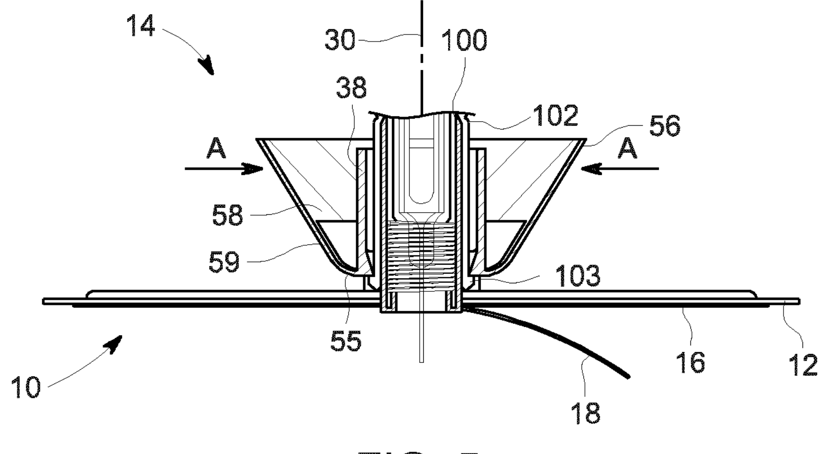
FIG. 5 shows a cross-sectional side view of a pad and part of an autoinjector.
Figure 6:
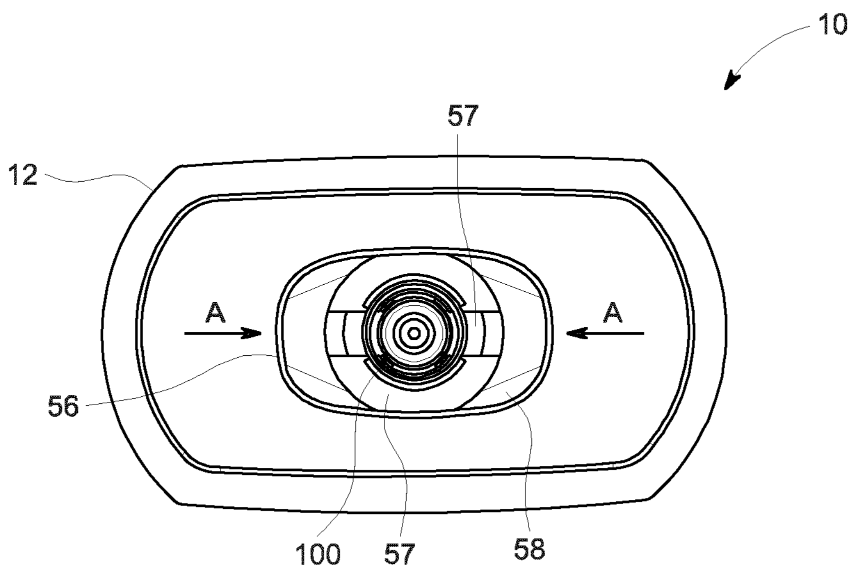
FIG. 6 shows a cross-sectional view in the proximal direction of the pad and autoinjector in FIG. 5.
Figure 35:
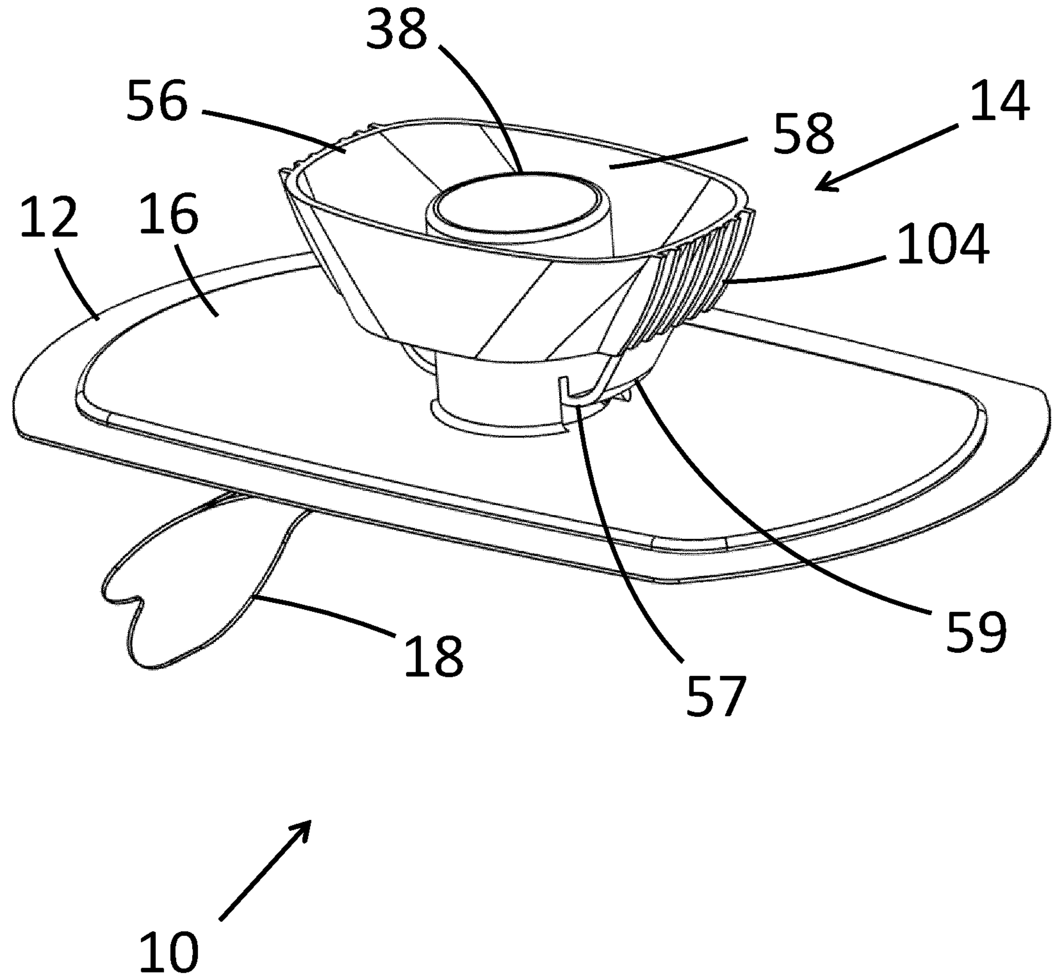
FIG. 35 shows a perspective view of the pad of FIGS. 5 and 6.

FIGS. 5, 6 and 35 show another example of a pad 10 with a corresponding autoinjector 100. As with the previous examples, the pad comprises an attachment portion 14 and an adhesive portion 16 comprising a flange 12, an adhesive and an adhesive portion cover 18. The attachment portion 14 comprises an autoinjector engagement portion 55 and a user manipulation portion 56. The attachment concept in this example unlocks in a similar fashion to some types of childproof bottle caps.

The attachment portion 14 can also optionally comprise a tubular portion 38 extending from the autoinjector engagement portion 55, although as can be seen in FIG. 6, the tubular portion 38 would typically not extend the whole way around the axis. The autoinjector engagement portion 55 engages the attachment portion of the autoinjector 100. The autoinjector 100 comprises a housing 102 and a protrusion 103 on the housing.

The user manipulation portion 56 comprises an elliptical conical section 58 which is flexible and is elliptical in the plane perpendicular to the axis 30. It also comprises arms 59 which attach the elliptical section (which is at the distal end of the attachment portion in this example) to the autoinjector engagement portion 55.

Whilst the elliptical conical section 58 of the user manipulation portion 56 extends around the entire circumference around the position where the autoinjector is placed during use, the autoinjector engagement portion 55 comprises two separate engagement sections 57. When the part of the ellipse further from the axis is pressed (as per arrows A in FIGS. 5 and 6), this makes the ellipse rounder, resulting in the minimum diameter of the ellipse increasing. This pulls the arms 59 and correspondingly the autoinjector engagement portion 55, more particularly the engagement sections 57 of the autoinjector engagement portion 55, further away from the axis 30. As a result, the engagement sections 57 are disengaged from the protrusion 103 on the autoinjector 100.

The shape of the various parts of the attachment portion in FIG. 5 could be varied. For example, the user manipulation portion just needs to able to be flexed to change its shape and thereby disengage the engagement section. This can be achieved by providing an elliptical ring instead of the elliptical conical section of the user manipulation portion 56. This could also be achieved by a circular user manipulation portion, with the user manipulation portion becoming elliptical when pressed, or with other shapes of user manipulation portion. Two engagement sections 57 are provided, but one or more engagement sections could be provided. Similarly, two arms 59 are provided, but one or more arms 59 could be provided. The particular shape of the engagement section could also be varied depending on the shape of the corresponding medicament delivery device and on the number of protrusions or grooves on the corresponding medicament delivery device. Instead of a protrusion-groove approach, a different attachment mechanism could be used; for example, a friction lock could alternatively be provided.

The method of use of the example in FIGS. 5 and 6 will now be described in more detail. As with the example in FIGS. 1 and 2, the optional adhesive portion cover 18 is first removed from the pad. The adhesive portion is then attached to the injection site. Once the pad is in place at the injection site, an autoinjector is inserted into the attachment portion 14, to the position shown in FIG. 5. At this point, the autoinjector engagement portion 55 of the attachment portion 14 locks the autoinjector in place, and the injection can proceed without the autoinjector being held, as with the previous examples. Once the injection has finished, the autoinjector is released by pressing at points A as shown on FIGS. 5 and 6.

Figure 7:
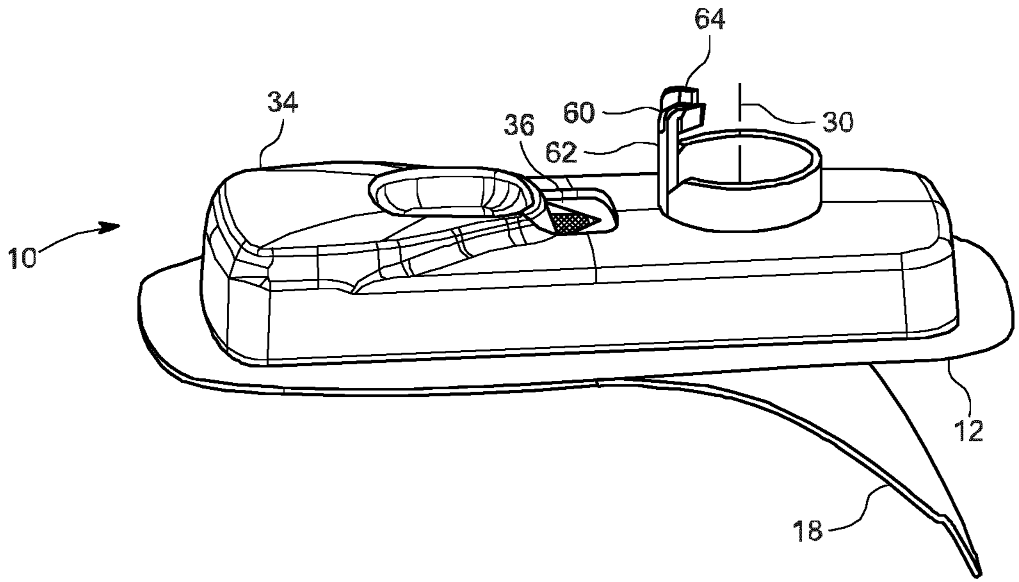
FIG. 7 shows a perspective view of a pad.

FIG. 7 shows another example of a pad 10, the pad comprising an adhesive portion 16 comprising a flange 12, an adhesive (not shown) and an adhesive portion cover 18, and an attachment portion comprising a housing 34, a slider 36 and an attachment arm 60. The slider 36 can move relative to the housing 34. The attachment arm 60 is attached to the slider and comprises an arm portion 62 and a protrusion 64. The shape of the attachment arm is designed to engage a window of an autoinjector, such as the window 106 in the autoinjector 100 in FIG. 1. In general, engaging an existing feature of an autoinjector such as the window of an autoinjector can allow a pad to be used with an existing autoinjector without any change to the structure of the autoinjector.

The method of use of the example in FIG. 7 will now be described in more detail. As with the previous examples, the optional adhesive portion cover 18 is first removed from the pad. The adhesive portion is then attached to the injection site. Once the pad is in place at the injection site, an autoinjector is inserted into the attachment portion 14. The slider is then moved towards the axis 30 so that a feature of the autoinjector such as a window (or more specifically the frame of the window in this case) engages with the protrusion 64, locking the autoinjector in place. The injection can proceed without the autoinjector being held. Once the injection has finished, the slider can be moved back away from the axis 30, thereby disengaging the protrusion 64 from the autoinjector and allowing the autoinjector to be removed.

In another example, the slider 36 is removed from the example in FIG. 7, and the attachment arm 60 is instead attached directly to the housing 34. The arm portion 62 of the attachment arm 60 is flexible, allowing the attachment arm 60 to be pushed aside when entering the autoinjector into the pad 10. Once the autoinjector is in place in the pad, the attachment arm will flex back, with the protrusion engaging the autoinjector (for example the window of the autoinjector). When the injection has been completed, the autoinjector can then be removed by the user flexing back the attachment arm, disengaging the autoinjector from the pad.

In general, the attachment arm 60, the arm portion 62 and the protrusion 64 can vary in shape, length and material in different examples, depending for example on the particular shape of the medicament delivery device (or devices) that the pad is designed to be used with.

FIGS. 8 to 13 show a further example of a pad 10. In this example, the pad 10 is part of a needle guard 112 (or more generally of a medicament delivery member guard). Although the pad 10 of FIGS. 8 to 13 is shown as part of the needle guard of an autoinjector, this type of pad structure/attachment structure could also be used with the pad as a separate component—that is, the attachment concept shown in FIGS. 8 to 13 would also work with a pad that is not an integral part of a needle shield.

Figures 8, 9, 10, 11:
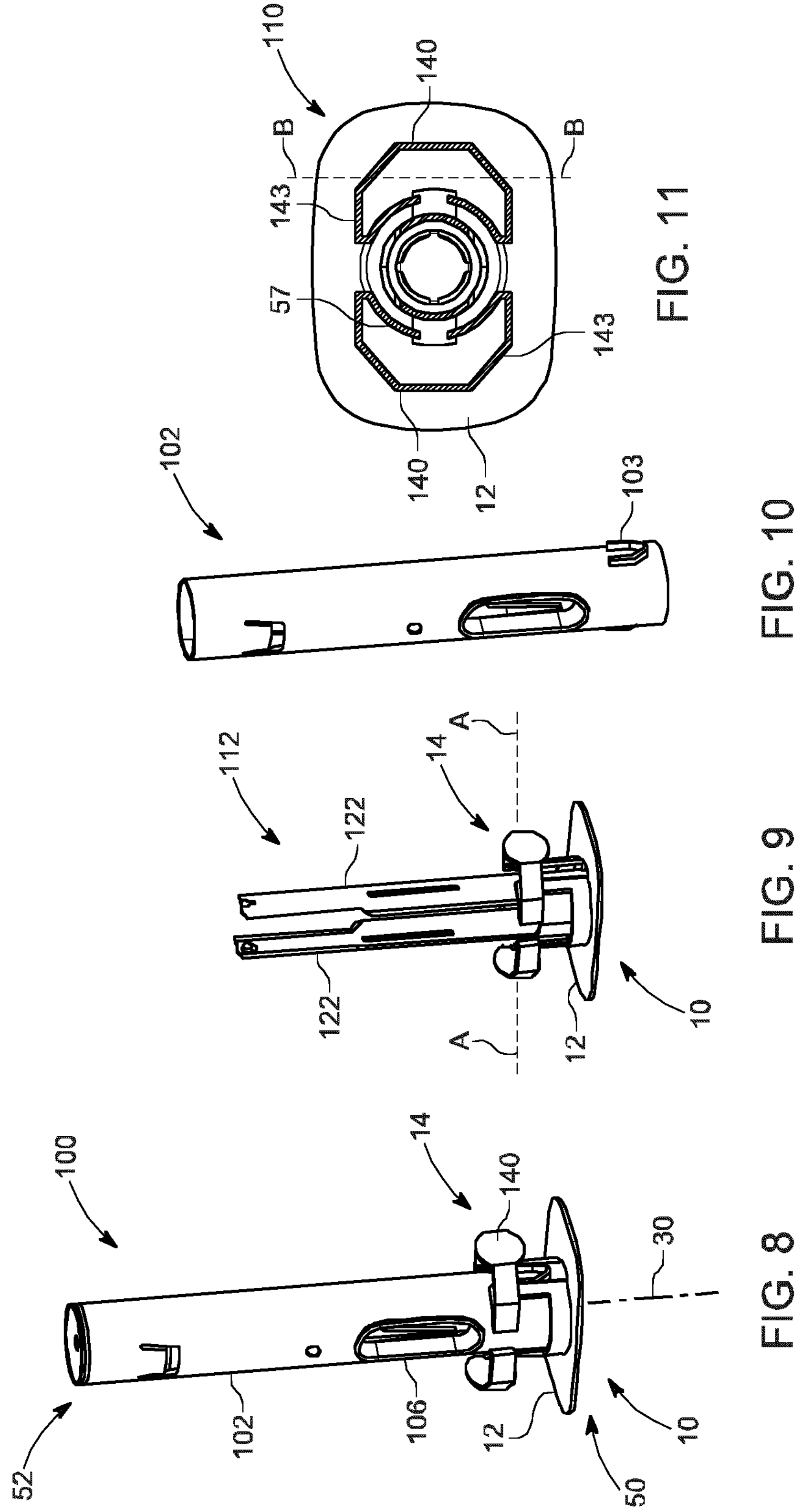
FIG. 8 shows a perspective view of an autoinjector comprising a pad.
FIG. 9 shows a perspective view of the needle guard of the autoinjector of FIG. 8.
FIG. 10 shows a perspective view of the housing of the autoinjector of FIG. 8.
FIG. 11 shows a cross-sectional view in the proximal direction from the plane A-A of the needle guard in FIG. 9.

FIG. 8 shows an autoinjector 100 comprising a housing 102, a window 106, and a pad 10. Apart from the pad 10, most of the rest of the needle guard is hidden in the housing 102 in FIG. 8. The needle guard 112 is shown in FIG. 9, with the needle guard 112 comprising the pad 10 and two needle guard arms 122. FIG. 10 shows the housing 102, which comprises an attachment portion, namely two protrusions 103 in this example, which is configured to attach (typically to releasably attach) the autoinjector 100 to the pad 10.

FIG. 11 shows a view from the plane A-A of FIG. 9, looking towards the proximal end 50. In particular, the shape of the attachment portion of the pad 10 can be seen. The attachment portion of the pad 10 comprises two handles 140, which are configured so that pressing the two handles towards each other releases the attachment portion from the protrusions 103 (i.e. from the attachment portion of the autoinjector). The handles 140 are each connected by an arc 143 that is shaped so that pushing a handle 140 towards the axis 30 pulls a corresponding engagement section apart, widening the gap between two protrusions 141 of the engagement section (see FIGS. 12 and 13).

Figures 12, 13:
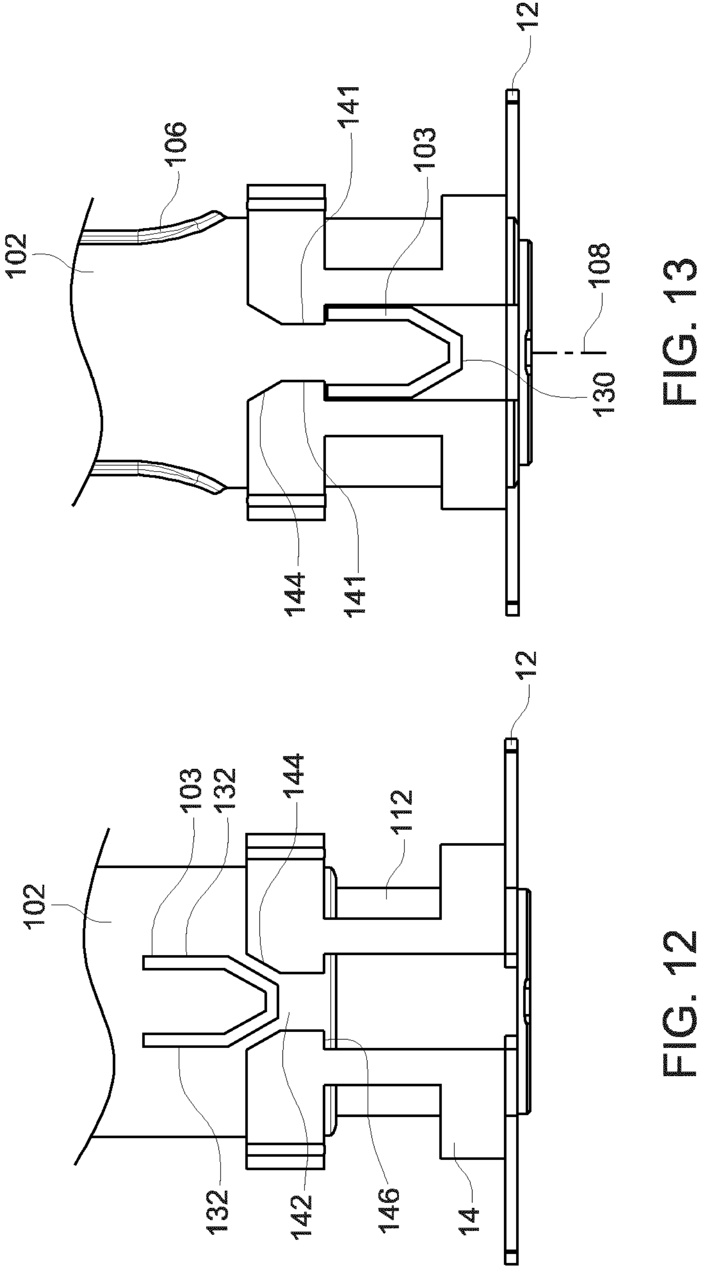
FIG. 12 shows a partial cross-sectional side view of the autoinjector of FIG. 8 along the plane B-B of FIG. 11, looking towards the axis.
FIG. 13 shows the same view as FIG. 12, but with the attachment portions of the housing and the pad attached to one another.

FIGS. 12 and 13 show a view from the plane B-B of FIG. 11, looking towards the axis. From this view, the attachment points can be seen between the attachment portion of the pad and the attachment portion of the housing, without the handles 140 being in the line of sight.

FIG. 12 shows the needle guard 112 extended, with the needle therefore not being visible. FIG. 13 shows the needle guard 112 retracted, with the result that only the pad 10 is visible in FIG. 13, including the flange 12 and the attachment portion 14.

In the view shown in FIGS. 12 and 13, the details of the protrusion 103 on the housing 102 can be seen, with the protrusion 103 comprising a V-shaped portion that protrudes from the housing. The protrusion 103 can be considered as the attachment portion of the autoinjector in this case. The centre 130 of the V-shaped portion is closer to the proximal end of the autoinjector than the two ends 132 of the V-shaped portion. The attachment portion 14 of the pad has a corresponding opening 142 that has two tapered edges 144 to allow the V-shaped portion to move in the proximal direction and push the two tapered edges 144 apart. The tapered edges are further apart from each other at the distal end of the tapered edges than at the proximal end of the tapered edges.

Once the V-shaped portion has moved past the opening 142, the two tapered edges 144 can move closer to each other again as they are no longer being biased apart by the V-shaped portion. The attachment portion 14 also has two proximal facing surfaces 146 at the proximal end of the tapered edges and on either side of the opening 142; these proximal facing surfaces 146 stop the V-shaped portion from moving back in the distal direction by engaging with the distal ends of the two ends 132 of the protrusion 103 (unless the handles 140 are pressed towards each other to disengage the attachment portions 14, 103 of the housing 102 and the pad 10 from each other). Pressing the handles 140 towards each other pulls the two proximal facing surfaces 146 away from each other, increasing the size of the opening 142 and removing the engagement between the two proximal facing surfaces 146 and the distal ends of the two ends 132 of the protrusion 103, thereby allowing the protrusion 103 to move back in the distal direction (i.e. from the position in FIG. 13 back towards the position in FIG. 12).

As with the other components of the autoinjector such as the housing 102 and the window 106, the particular shape of needle guard arms 122 in FIG. 9 is not essential. The particular shape of needle guard arms (or more generally medicament delivery guard arms) described above is designed to interact with a rotator, such as the rotator in WO2011/123024. Other shapes and lengths of needle guard arms could be provided though, depending on the medicament delivery device and on the parts of the medicament delivery device that the medicament delivery member guard is designed to interact with.

The method of use of the example in FIGS. 8 to 13 is similar to the methods of use described above, although it is simpler in some ways due to the pad being integrated in the autoinjector. First, the pad 10 is placed against the injection site. Next, the autoinjector is pushed in the proximal direction by pushing the housing towards the injection site. This results in the needle guard retracting inside the housing (i.e. from the position in FIG. 12 to the position in FIG. 13). The needle 108 pierces the injection site and the injection commences (either automatically or after the user presses a button, as described in relation to the example in FIGS. 1 and 2 above). As with the examples above, the pad is adhered to the injection site, meaning that the injection can continue hands-free if desired. Once the injection has finished, the handles 140 are pressed to release the protrusion 103, resulting in the housing moving in the distal direction (i.e. from the position in FIG. 13 to the position in FIG. 12). The autoinjector can then be removed from the injection site. Alternatively, the step of removing the autoinjector from the injection site can be carried out before the step of pressing the handles 140, though this would mean that the needle is exposed from the time when the autoinjector is removed from the injection site until the handles are pressed towards each other.

Instead of an attachment portion as shown in the example in FIGS. 8 to 13, a different attachment portion could be provided as part of the medicament delivery member guard. To give one example, an arm similar to the arm 60 in FIG. 7 could be provided instead of the attachment portion in FIGS. 8 to 13. In such an example, there would also be no need to provide an attachment portion 110 on the housing.

Figures 14, 15, 16:
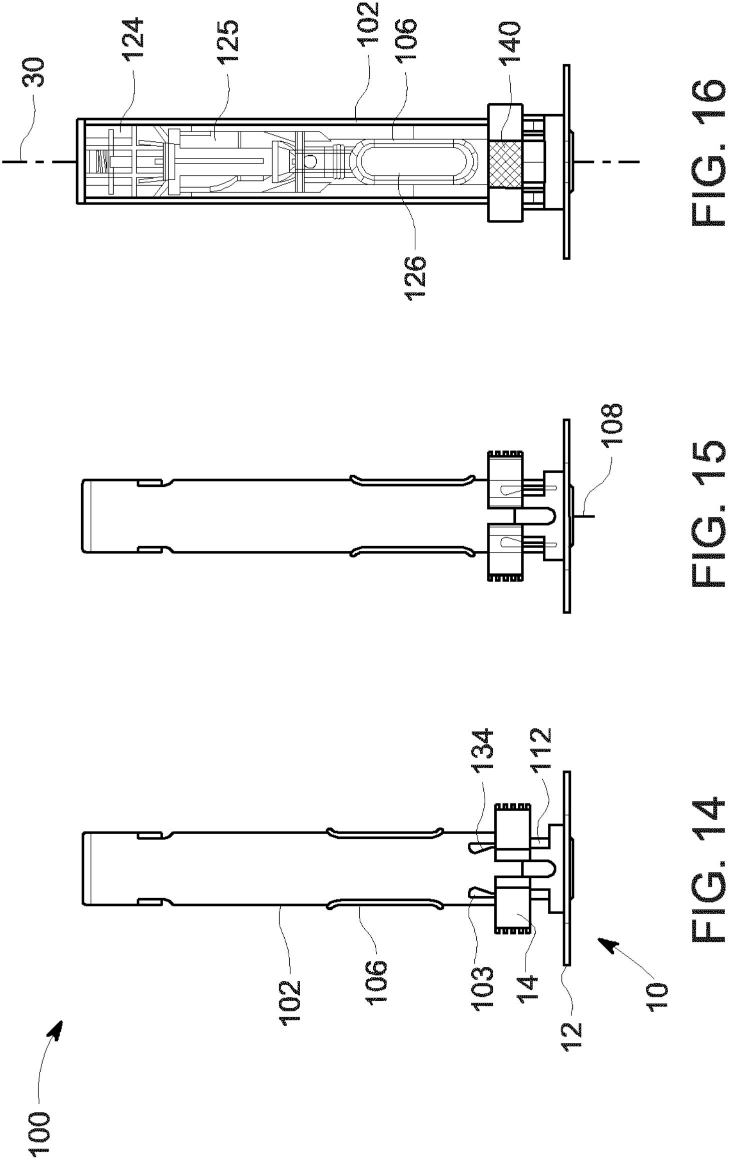
FIG. 14 shows a side view of an autoinjector comprising a pad.
FIG. 15 shows a side view of the autoinjector of FIG. 14, with the position of the attachment portions of the housing shown behind the pad.
FIG. 16 shows a different side view of the autoinjector of FIG. 14, with the pad shown fully but the housing shown in cross-section.
Figure 17:
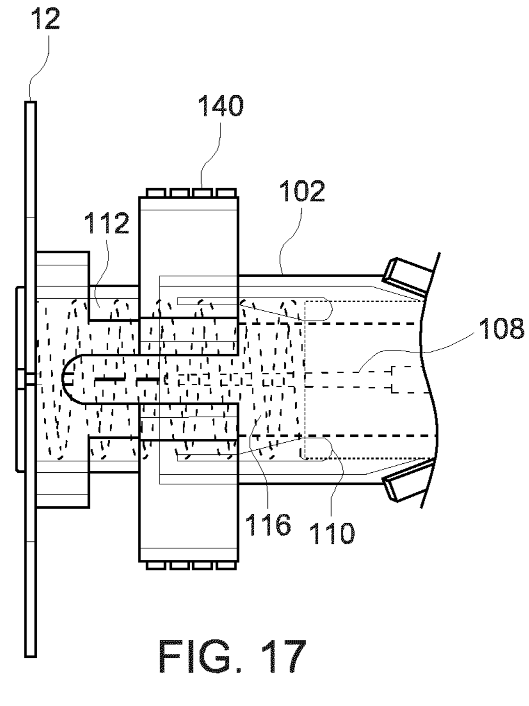
FIG. 17 shows a side view of part of the autoinjector of FIG. 14.
Figure 18:
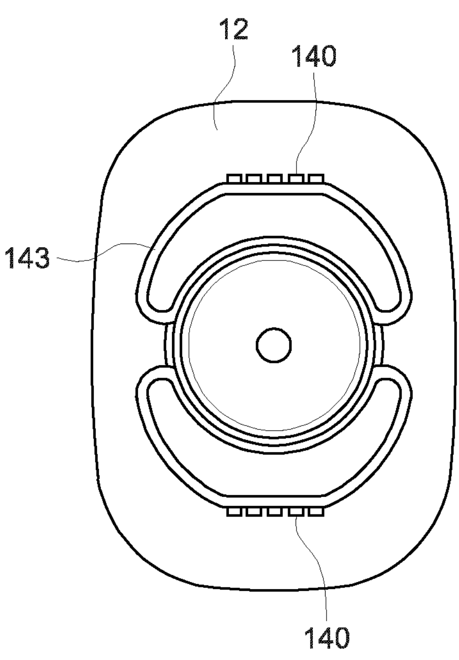
FIG. 18 shows a cross-sectional view in the proximal direction of the autoinjector of FIG. 14.
Figure 19:
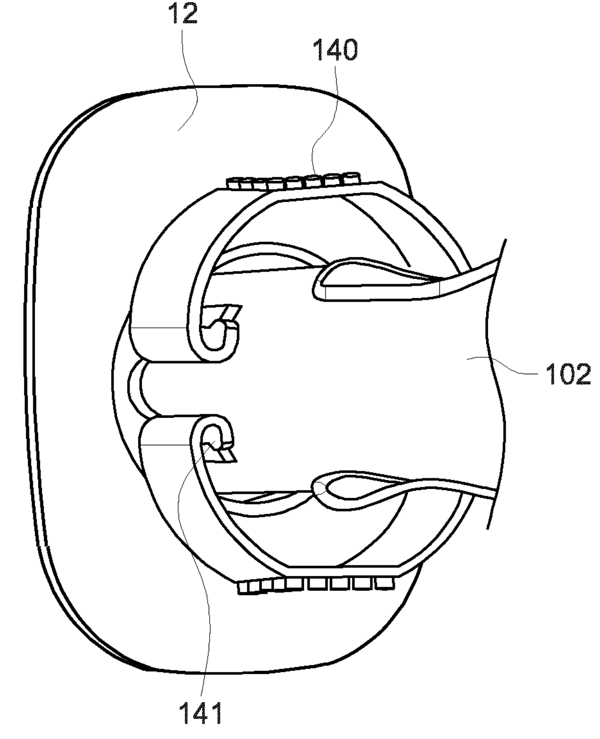
FIG. 19 shows a perspective view of part of the autoinjector of FIG. 14.

FIGS. 14 to 19 show another example similar to the example in FIGS. 8 to 19, which will now be described with particular reference to FIGS. 14 and 17, which show the needle guard in an extended state, and to FIGS. 15 and 19, which show the needle guard in a retracted state.

FIG. 14 shows an autoinjector 100 comprising a housing 102, a window 106, two protrusions 103 (i.e. an attachment portion of the housing 102) and a pad 10, where the pad comprises a flange 12, an attachment portion 14 and an adhesive (not shown). FIG. 15 shows the autoinjector with the needle guard retracted and the position of the protrusions 103 shown inside the pad 10. The two protrusions are spaced apart from one another in the circumferential direction.

FIG. 16 shows the needle guard retracted as in FIG. 15, and is a view 90 degrees rotated around the axis 30, so that the window 106 and the handle 140 are shown in front rather than at the side. The housing 102 is shown in cross-section so that various features of an example autoinjector are shown, although other internal features would also be possible. In particular, a rear housing 124, a rotator 125 and a medicament container 126 can be seen, although these are again just shown for context and the specific structure shown is not essential.

FIGS. 17 to 19 provide a closer view of the pad 10 and the proximal end of the autoinjector 100 more generally, with several parts again shown inside the autoinjector in FIG. 17 to show internal components. The protrusion 103 of the autoinjector 100 and the attachment portion 14 of the pad 10 are somewhat differently shaped, but in general the parts, even if differently shaped, are generally equivalent to those shown in FIGS. 8 to 13 above. The method of use is also basically as described above for FIGS. 8 to 13.

Turning back to FIGS. 14 and 17 in particular, each of the protrusions 103 comprises a rib extending in the axial direction. Each protrusion comprises an angled surface 134 that extends in both the axial and circumferential directions. The protrusions are closer together at their distal end than at their proximal end—that is, the gap between a distal portion of the protrusions is smaller than the gap between a proximal portion of the protrusions. The angled surfaces 134 are arranged to guide a corresponding pair of protrusions 141 on the engagement section of the attachment portion 14 of the pad 10.

A method of use of the autoinjector of FIGS. 14 to 19 will now be described. The pad is first attached to the injection site. The housing 102 is then pushed in the proximal direction (towards the injection site). As the housing moves in the proximal direction, the protrusions 141 on the engagement section of the attachment portion of the pad engage with the angled surfaces 134 on the protrusions 103 on the housing. This pushes the protrusions 141 on the engagement section of the attachment portion of the pad towards each other. When the housing is pushed to its furthest extent in the proximal direction, as shown in FIG. 15 for example, the protrusions 141 on the engagement section of the attachment portion of the pad are further from the injection site than the protrusions 103 on the housing 102—that is, they have passed beyond the protrusions 103 on the housing 102 and are therefore free to move further apart again. At this point, the housing 102 cannot move back in the distal direction because the protrusions 103 on the housing 102 engage with the distal end of the protrusions 141 on the engagement section of the attachment portion of the pad.

Once the housing is locked in place, the injection can begin-automatically in the example given, although this general approach to locking the autoinjector in place could be used on other autoinjectors or other medicament delivery devices. Once the injection is finished, the housing 102 can be disengaged from the pad 10 by pushing the handles 140 together (either before or after the pad is removed from the injection site), allowing the housing to move back in the distal direction relative to the pad.

Figure 20:
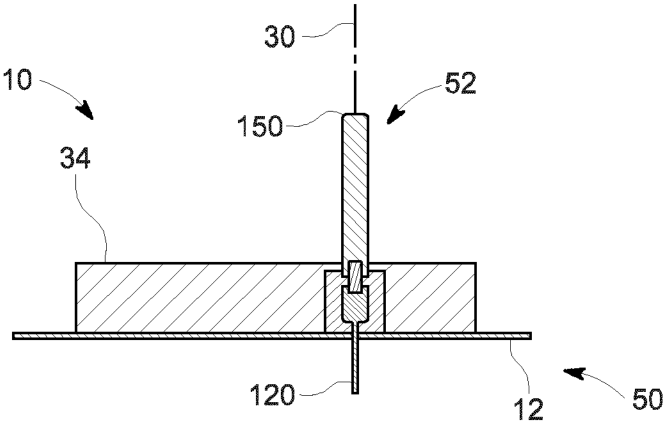
FIG. 20 shows a diagram of a pad and a medicament delivery device.

FIG. 20 shows another example of a pad 10. The pad 10 comprises an adhesive portion comprising a flange 12. The pad 10 also comprises an attachment portion. The attachment portion is not shown in detail, but comprises a housing 34. Alternatively or additionally to the housing 34, an attachment portion such as those described in FIG. 1, 3, 5 or 7 could be used. The pad also comprises a medicament delivery member 120 such as a needle or a cannula, which would typically be flexible.

Concerning the method of use, the pad is first attached to the injection site using the adhesive pad. The medicament delivery member is inserted into the injection site either during or after attachment of the pad to the injection site. A medicament delivery device such as an autoinjector would then be attached to the pad, following which the injection could commence. After the injection has finished, the medicament delivery device can optionally be removed as described in the previous examples.

Several options are available in terms of the connection between the autoinjector and the medicament delivery member of the pad. For example, the medicament delivery member of the pad could engage directly with a medicament delivery member of the medicament delivery device. Alternatively, the medicament delivery device may be lacking a medicament delivery member entirely, in which case the primary package (the medicament container) in the medicament delivery device could connect directly to the pad.

Figure 21:
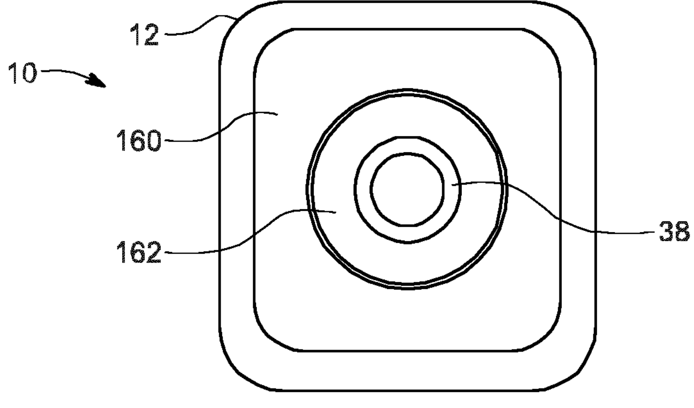
FIG. 21 shows a view in the proximal direction of a pad.
Figure 22:
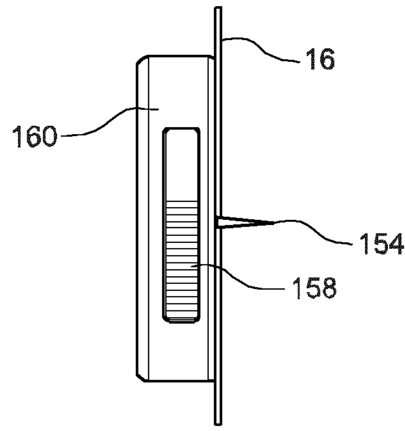
FIG. 22 shows a side view of the pad of FIG. 21.
Figure 23:
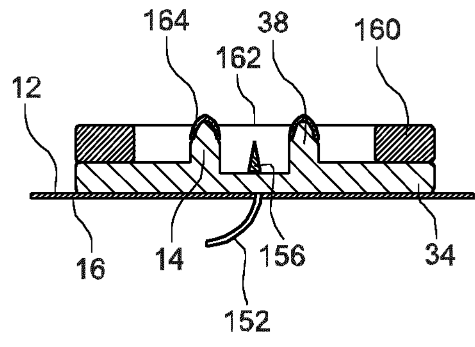
FIG. 23 shows a cross-sectional side view of the pad of FIG. 21.

FIGS. 21 to 23 show another example of a pad 10 similar to the pad in FIG. 20. The pad 10 comprises a flange 12, an attachment portion 14, an adhesive portion 16, a housing 34, a cannula 152 and a cannula insertion needle 154. The attachment portion 14 comprises a medicament delivery device insertion needle 156, an activation button 158 for inserting the cannula insertion needle 154 into the injection site, an optional outer housing 160, an optional compressible pad 162, a tubular portion 38 and optional padding 164 on the distal end of the tubular portion.

Figure 24:
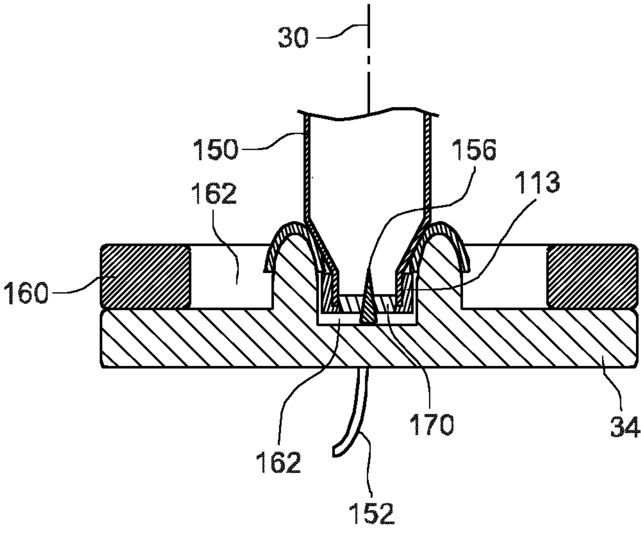
FIG. 24 shows a cross-section side view of a pad and part of a medicament delivery device.

FIG. 24 shows another example of a pad 10 without a flange but otherwise similar to the pad in FIGS. 21 to 23. The pad 10 is shown with a medicament delivery device 150 attached to the pad 10. In this case the medicament delivery device 150 is a cartridge with a membrane 170 and a plunger 172 (see FIG. 28, for example). The medicament delivery device insertion needle 156 is shown penetrating through the membrane 170. A membrane guard 113 is also shown; this would function in a similar way to the medicament delivery member guards described elsewhere in the application in that the membrane guard is initially in an extended position, typically to protect the membrane from being pierced before use, and moves to a retracted position to expose the membrane. That is, when the cartridge is pushed against the pad, the membrane guard 113 is pushed in the distal direction relative to the rest of the cartridge. On the pad 10, the compressible pad 162, which is initially in an uncompressed state before a cartridge is attached (FIG. 23), is compressed by the cartridge being attached (FIG. 24). The compression of the compressible pad 162 exposes the medicament delivery device insertion needle 156, which pierces the membrane 170. A medicament delivery member guard typically extends again after injection; in contrast, the membrane guard does not need to extend again to guard a medicament delivery member such as a needle after injection. The compressible pad 162 could also expand back to its original state after the cartridge is removed; this could be useful in particular if the pad is reuseable, so as to help protect the needle 156 between injections. An extra cap could additionally or alternatively be provided to cover the needle 156.

Figures 25, 26, 27:
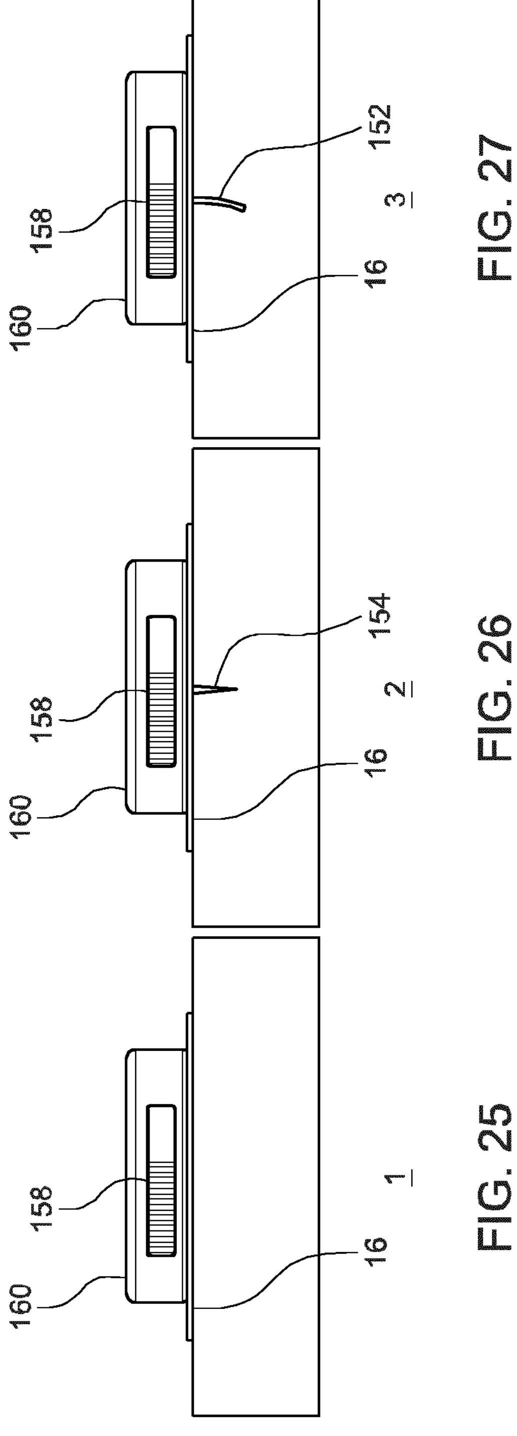
FIGS. 25, 26 and 27 show a side view of the pad of FIG. 21 in different stages of attachment to an injection site.
Figures 28, 29:
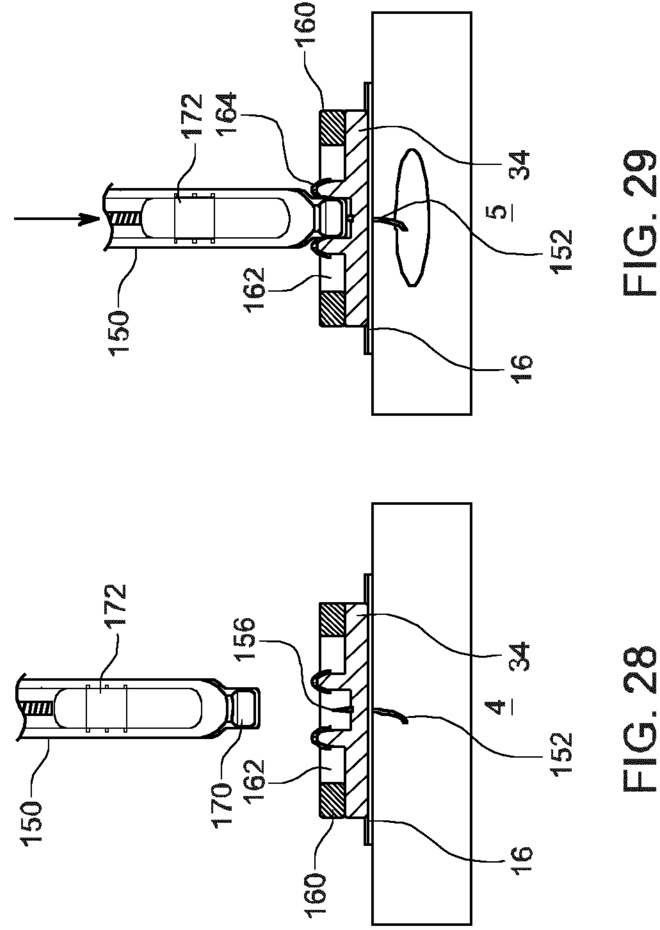
FIG. 28 shows a cross-sectional view of the pad of FIG. 21 and a medicament delivery device before medicament delivery.
FIG. 29 shows a cross-sectional view of the pad of FIG. 21 and a medicament delivery device during a medicament delivery.
Figure 30:
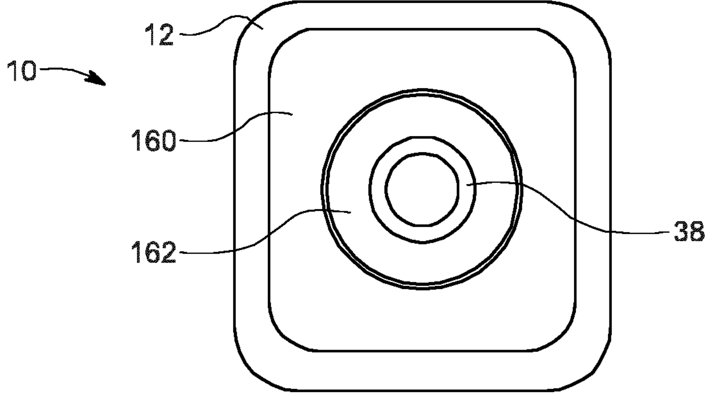
FIG. 30 shows a view in the proximal direction of a pad.
Figure 31:
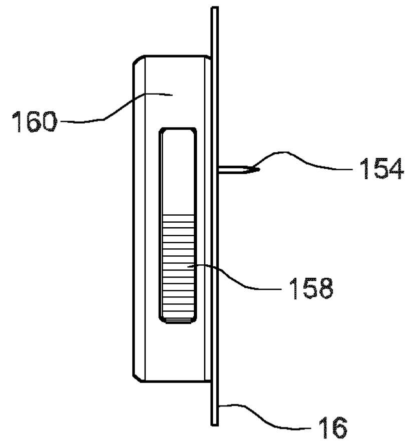
FIG. 31 shows a side view of the pad of FIG. 30.

An example method of use of the pads of FIGS. 21 to 24 is now described with reference to FIGS. 25 to 29, using the pad 10 shown in FIGS. 21 to 23. Firstly, in FIG. 25, a pad 10 is attached to the injection site. Secondly, in FIG. 26, the cannula insertion needle 154 is inserted into the injection site, thereby inserting the cannula (now shown in FIG. 26). The cannula insertion needle 154 is then retracted, leaving the cannula in the injection site as shown in FIG. 27. The medicament delivery device 150 is then attached to the pad 10 and the medicament is injected (FIGS. 28 and 29).

FIGS. 30 to 33 show another example of a pad 10, similar to the examples in FIGS. 21 to 29. In contrast to the examples in FIGS. 21 to 29, the cannula insertion needle 154 is offset from the axis 30 (i.e. the axis on which the medicament delivery device is centred, which is also the axis running through the centre of the attachment portion of the pad as a result). In other words, in the axial direction, the cannula insertion needle 154 (and the cannula 152) are offset from the medicament delivery device insertion needle 156.

The method of use of the example pad in FIGS. 30 to 33 is similar to the examples in FIGS. 21 to 29. The pad 10 is attached to an injection site, and the cannula 152 is inserted using the cannula insertion needle 154. The medicament delivery device 150 is then attached to the attachment portion 14 of the pad 10 (though this step could alternatively happen before insertion of the cannula 152). The injection can then proceed. Once the injection is completed, the medicament delivery device can be removed from the pad.

Figure 33:
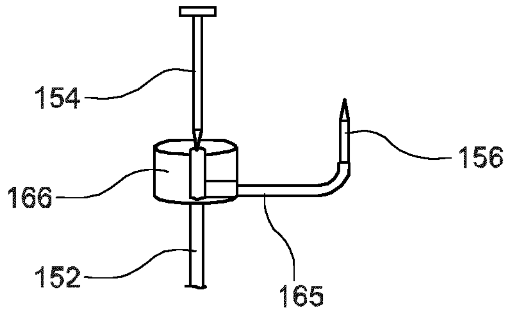
FIG. 33 shows a close-up of features within the pad of FIG. 30.

A close-up of an example of the features around the cannula 152, the cannula insertion needle 154 and the medicament delivery device insertion needle 156 is shown in FIG. 33. In this particular example, the medicament delivery device insertion needle 156 is connected to the connection hub 166 by a tube 165. The cannula 152 is also connected to the connection hub 166. The mechanism is set up so that a fluid can flow from the medicament delivery device into the injection site via the medicament delivery device insertion needle 156, the tube 165, the connection hub 166 and the cannula 152. A cap (not shown) could be provided to cover the medicament delivery device insertion needle when not in use. A cannula insertion needle 154 is provided to insert the cannula 152 into the injection site. At its simplest, the cannula insertion needle 154 could be inserted (and also retracted if required) manually, for example by a user directly pushing a cannula insertion needle. However, it is generally preferable that this process is automated, and that an activation button 158 is used to insert the cannula insertion needle and the cannula. Such activation systems are not described in detail in this application, but appropriate mechanisms can be found described in existing literature, with one example being shown in WO 2020/058069, which is incorporated herein in its entirety by reference.

Figure 34:
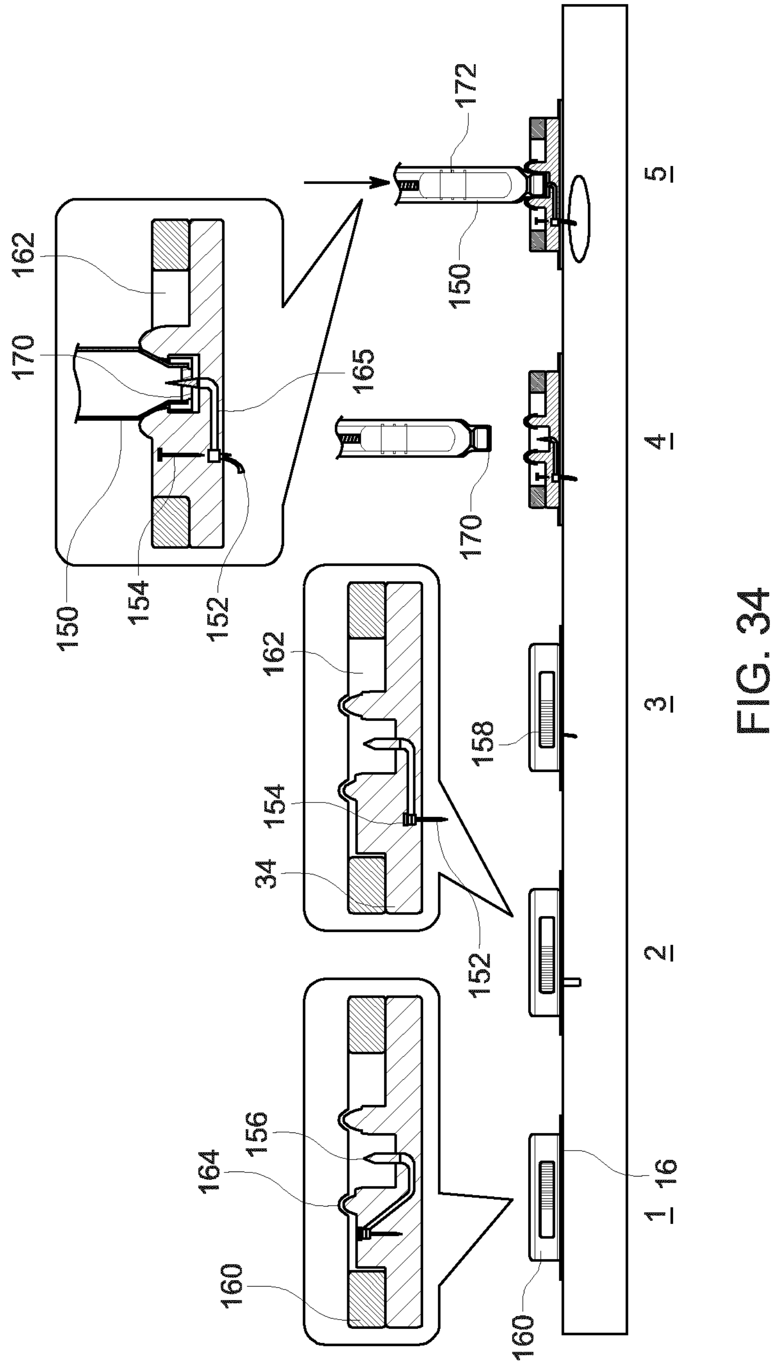
FIG. 34 shows side and cross-sectional views of the pad of FIG. 30 and a medicament delivery device in various stages of injection.

FIG. 34 shows the method of use of the example from FIGS. 30 to 33, which is similar to that of the examples in FIGS. 21 to 29 above to which reference should now be made—in brief, step 1 shows the pad 10 in its initial state after being attached to the injection site. Step 2 shows the pad with the cannula insertion needle 154, and therefore also the cannula 152, inserted into the injection site. Step 3 shows the pad with the cannula insertion needle 154 (and the cannula still inserted into the injection site). Step 4 shows a medicament delivery device 150 approaching the pad 10. Step 5 shows the medicament delivery device and pad during injection.

Some of the pads 10 described herein are shown as part of a medicament delivery device such as an autoinjector (e.g. FIG. 8), and some of the pads are standalone devices (e.g. FIG. 5) that can be attached to a medicament delivery device such as an autoinjector. In general, though, the pads that are described as standalone devices could also be provided as part of a medicament delivery device such as an autoinjector.

As already alluded to above in reference to some of the examples, in general the pad could be designed to work with a particular type of autoinjector or medicament delivery device or a particular group of autoinjectors or medicament delivery devices, or could be designed to work with as many different medicament delivery devices as possible. For example, a pad could be designed to only work with a specific autoinjector or medicament delivery device, or the pad could be designed to allow many different autoinjectors or medicament delivery devices to be used with the pad. Where examples using autoinjectors are described herein, medicament delivery devices more generally could alternatively be used.

In some cases, the pad may be designed to work with an unmodified existing medicament delivery device (e.g. FIG. 7). Alternatively, the structure of the medicament delivery device may be amended as well-though often only the medicament delivery guard and/or the housing (outer housing) of the medicament delivery device would need to be modified. Other parts of the autoinjector may also be modified. The autoinjectors depicted in the Figures are all cylindrical in cross section, but other cross sections, such as triangular, could also work, for example with an appropriate change in the pad design.

In general, a flange 12 as shown in many of the examples is not essential, and the adhesive may be attached directly onto another part of the pad, for example an attachment portion, a housing and/or a medicament delivery member guard. Nevertheless, it can be advantageous to include a flange, typically a flexible flange, to increase the area of the adhesive portion. The flange is typically planar, but other shapes are also possible, for example a shape that mirrors the expected contours of a body part on which the pad is designed to be attached, for example a portion of the thigh or of the lower abdomen. Following body contours—with the shape of the flange itself and/or by providing a flexible flange—can provide better adhesion. The flange is typically attached to the attachment portion of the pad.

The flange is generally described herein as extending away from the attachment portion relative to the axis 30, but the flange can alternatively or additionally extend closer to the axis than the attachment portion. A hole could be left for a medicament delivery member such as a needle to extend through, or the flange could extend fully across the proximal end of the pad, with the flange configured to be pierced by the medicament delivery member.

Numerous different options are possible for the attachment portion 14, and the examples above already show and describe a variety of such options. Such options are generally transferable between the various different examples—as one example, the general attachment portion concept in FIG. 4 or in FIG. 8 could be incorporated into a pad according to FIG. 21. A number of other different attachment portion concepts are not directly shown in the Figures but are also mentioned above with respect to the examples, for example the example in FIGS. 1 and 2, and these concepts could equally be incorporated in the other examples described herein. In general, numerous different elements could be used, either individually or in combination, to provide an attachment portion, including hooks, protrusions, friction locks, snap-fit locks, sliders or the like. In the case of a friction lock, the corresponding surfaces of the attachment portions of the pad and/or the medicament delivery device could be coated a with high friction material or roughened up so that the surfaces provide enough friction to hold the medicament delivery device in place in the pad.

The adhesive portion 16 generally comprises an adhesive portion attached to the pad, for example to the flange and/or to the medicament delivery member guard. The adhesive portion optionally comprises a flange as described above. The adhesive portion is generally at the proximal-most end of the pad (or of a medicament delivery device, for example an autoinjector, in examples where the pad is part of the medicament delivery member guard). The adhesive portion is generally a substance such as glue, but could alternatively be another means of attachment of the pad to the injection site. For example, a strap could be provided instead of an adhesive. Heat staking could also be used to attach the adhesive portion to the injection site.

An adhesive portion cover 18 is optionally provided to protect the adhesive surface until shortly before use of the pad. The adhesive portion cover can extend as far as the adhesive, or can extend a different amount, for example further than the adhesive, with an extra protrusion for ease of removal, as shown in FIG. 1 for example.

Some examples include a housing 34, which can serve various purposes, such as supporting an adhesive layer, supporting a flange, supporting a locking and/or releasing mechanism such as the release button 20 in FIG. 1 or the slider 36 in FIG. 3, housing an attachment portion such as in FIG. 23, and/or housing a medicament delivery member such as the cannula 152 in FIG. 34. The shape of the various housings shown in the Figures are just shown as examples and can be varied, for example to optimise usability, to accommodate differently shaped medicament delivery devices, and/or to accommodate different attachment or adhesive portions of the pad.

Some examples (e.g. FIGS. 3 and 7) include a slider 36 that is typically at least partly within the housing of the pad. Various alternative shapes for the slider are possible, with several examples already provided above. The slider is generally configured to slide in the radial direction, though an alternative where the slider moves in a different way to engage and disengage, for example in the circumferential direction, is also possible.

The attachment portion 14 of the pad 10 typically includes a tubular portion 38 extending in the axial direction (for example FIG. 5). The proximal end of an autoinjector can sit in the tubular portion, preferably with a snug fit between the tubular portion and the autoinjector, to help support the autoinjector. Although a tubular portion of some kind is shown in the examples in many of the Figures, the provision of a tubular portion is optional in each example.

A number of medicament delivery devices are described herein, including those shown from FIG. 20 onwards. The medicament delivery device may be an autoinjector, a pen injector or a cartridge, for example. In particular, the medicament delivery device may or may not comprise a pad as an integral part of the medicament delivery device, and it may or may not comprise a needle as part of the medicament delivery device.

An autoinjector may be defined as a medicament delivery device in which at least one of the steps of the injection process is automated. For example, at least one of the steps of needle insertion, injection of a medicament or needle removal is automated (as opposed to all the steps having to be done by a user, as is the case in a traditional syringe).

Various different examples of an autoinjector 100 are described herein, particularly with reference to FIGS. 1 to 19, although these examples are not intended to be exhaustive. An autoinjector is a type of medicament delivery device, and in general whenever the phrase 'medicament delivery device' is used herein, an autoinjector is an example of the medicament delivery device. More detail on one example of an autoinjector can be found in WO2011/123024, which is incorporated herein in its entirely by reference. Some of the concepts, examples and alternatives described herein are described with reference to an autoinjector as an example, but these should not be considered to be limited only to being used with autoinjectors. In general, all the concepts, examples and alternatives described herein could be used with various medicament delivery devices, and not necessarily just with autoinjectors. The medicament delivery device could be a single-use or multi-use device, for example a single-use autoinjector or a multi-use autoinjector. That is, the medicament delivery device may provide a single fixed dose, a variable dose, or multiple doses.

Several of the examples show various features of an autoinjector. The housing 102 could be various shapes, for example with a triangular cross-section perpendicular to the axis rather than the circular cross-section of the example in FIG. 1, or with a semi-spherical distal end rather than a generally flat distal end as in FIG. 8. Various features of the autoinjectors described herein are optional, such as the slope 101, the grip 104 and the window 106.

In some examples, a protrusion 103 is provided on the housing 102. The protrusion 103 can be thought of more generally as an attachment portion. In the examples herein, two or four protrusions are shown, but one, three, five or more protrusions are also possible in other examples. The protrusion is shown on the outside surface of the housing, but the protrusion, or the attachment portion of the housing of the autoinjector more generally, could alternatively be on the inside surface of the housing, with a portion of the attachment portion of the pad extending inside the housing to engage the protrusion.

Some of the medicament delivery devices described herein include a medicament delivery member such as a needle 108. Where a particular example describes a needle, a medicament delivery member more generally could also be provided.

Some of the medicament delivery devices described herein include an attachment portion. The attachment portion is typically on the housing of the medicament delivery device, but could also be attached to a different part of the medicament delivery device, such as a guard, a grip or a window. The particular shape of the attachment portions shown herein (e.g. in FIGS. 12 and 14) could also be varied—the specific shape is not essential.

A number of the examples above include a guard, for example a medicament delivery member guard such as the needle guard 112 in FIG. 9. The membrane guard 113 in FIG. 24 is another example of a guard. The guard could interact with the pad. For example, the guard could also be used as part of the mechanism for removing the medicament delivery device from the pad. For example, once the plunger rod has moved fully forward (and as a result the injection is over), the plunger rod could physically release or disengage the pad from the medicament delivery device, either directly or via another part of the medicament delivery device. This would result in the medicament delivery device automatically releasing once the injection is finished. The release mechanism could release a needle guard spring 116 for example, with the plunger rod releasing the spring, and the spring then overcoming the lock (for example a friction lock) between the pad and the medicament delivery device).

In some examples, the pad comprises a medicament delivery member 120. The medicament delivery member 120 could be, for example, a needle or a cannula 152.

Some of the examples include handles 140 of the attachment portion of the pad. In each case, two handles are shown, although other numbers of handles, including just one, could be provided. In FIG. 8, for example, the handle 140 is shown with a smooth face, and in FIG. 16, for example, the handle 140 is shown with a grip (a contoured surface), but various surface textures are possible in either example. Instead of pushing on handles, some examples could be locked and unlocked by twisting in the circumferential direction, as also mentioned elsewhere herein.

Two examples of the structure attaching the handles 140 to the engagement section 57 are described, and can be seen particularly in FIGS. 11 and 18. FIG. 11 shows an angular arc 143 (when viewed perpendicular to the axis), whereas the arc in FIG. 18 is curved. The attachment portions can be amended in various ways, for example with the handle directly moving the engagement portion rather than through an arc 143, and/or with the handle offset in the circumferential direction from the engagement portion.

A number of features are shown in the examples in FIGS. 20 to 34; the structure of these features is focussed on examples of pads that include a medicament delivery member such as a cannula (e.g. a soft cannula/flexible cannula). However, many of the features described with reference to FIGS. 20 to 34 could also be used with the examples described with reference to FIGS. 1 to 19, particularly with respect to features such as the housing of the pad, the attachment portion of the pad, the activation button 158 and the compressible pad 162. The activation button 158 could take various forms instead of the slider button shown in the Figures. The activation button is shown on the outer housing 160 in FIG. 22 for example, but could be attached to other parts of the pad instead, such as the housing 34 of the pad. The outer housing 160, compressible pad 162 and padding 164 could also take various shapes other than those shown in the Figures or be removed entirely. Features from examples without a medicament delivery member could also be used in examples with a medicament delivery member—for example, the attachment portion of the pad described in FIG. 7 could be used with the pad of FIG. 24.

A number of methods of use have been described above. Further method alternatives will be described below, along with modifications to the apparatus that are relevant these methods. As already alluded to, a medicament delivery device such as an autoinjector may be removably attached to the pad, which allows for multiple uses of the same pad. Multiple uses could either be carried out by removing the pad from the injection site and then subsequently reattaching it at the same injection site or a different injection site, or by leaving the pad on the injection site in between injections. In cases where the pad is left on the injection site, it could be left on for a maximum amount of time or a maximum number of injections. Multiple uses could also be facilitated by a replaceable adhesive layer or by replacing the adhesive layer with a feature such as a strap as mentioned above.

An initial start of medicament delivery indication is typically provided by a tactile, visual or audible indication such as a click at the beginning and/or at the end of medicament delivery, as is mentioned above. When these indications are clicks, they are typically denoted as start and end clicks respectively. Instead of or in addition to being provided by the medicament delivery device, start and/or end indications could be provided by interaction between the medicament delivery device and the pad, or between two parts in the pad itself. For example, the initial indicator could be caused by the medicament delivery device and the pad engaging, for example with a click or a vibration. Regardless of where the indication is produced, a visual indicator could be alternatively or additionally provided on the medicament delivery device and/or the pad, for example a screen or a moveable indicator. For example, the attachment of the autoinjector to the pad could also complete a circuit, allowing a display of some kind on the pad or on the medicament delivery device to confirm visually that the injection has started, and/or allowing activation of an audible indication by means of a loudspeaker on the pad or in the medicament delivery device.

As an example, the corresponding attachment portions on the medicament delivery device and the pad snapping into place in the example in FIG. 8 could be used as a first click. In this case, the engagement of the attachment portion of the autoinjector with the attachment portion of the pad could provide the first click. More generally, this would be particularly relevant in examples where a click caused by the engagement of the attachment portion of the autoinjector with the attachment portion of the pad could occur at around the same time as the start of injection, for example in cases where injection is triggered by retraction of the needle shield.

A final click could also be caused by automatic release of a medicament delivery device from a pad, as described below.

After injection, one option is that the medicament delivery device could automatically disengage when the injection has finished—for example by disengaging when a guard such as a needle guard is released. For example, release of the needle guard could result in the force of the needle guard spring pushing a lock such as a friction lock hard enough that the lock effect from the friction is overcome, so that the autoinjector housing is pushed out of the tubular portion 38 of the pad. This would provide a visual indication that the injection is completed, and could provide an audible indication as well. Another example where the medicament delivery device automatically disengages could be created using the example in FIGS. 3 and 4. The arms 39 in the example in FIGS. 3 and 4 can be flexible. If the needle guard is locked back (i.e. so that there is no force pushing the needle guard out of the housing) until the injection is complete, the arms can then be flexed outwards once the needle guard is released, using the force of the needle guard spring to push the arms outwards and automatically release the needle guard shield.

In another alternative, a pad such as those described in FIGS. 20 to 34 comprises a needle instead of a cannula (meaning that a cannula insertion needle is also not required). Rather than the needle or cannula being inside the pad until after the pad is attached to the injection site, the needle could already extend beyond the main body of the pad (e.g. beyond the housing and/or beyond the adhesive layer), so that when the pad is attached to the injection site, the needle is also inserted into the injection site. Alternatively, a cannula and a cannula insertion needle are provided instead of the needle. The cannula and cannula insertion needle are inserted when the pad is attached at the injection site. The cannula insertion needle can then subsequently be retracted from the injection site, leaving the cannula (e.g. a soft cannula) in the injection site.

Pads that include a medicament delivery member can provide a relatively simple solution to the user compared to many existing solutions. When attaching the pad to the injection site, the pad can just be attached to the skin and the insertion activator, for example button 158, can be activated (e.g. pushed). There is no need for any further steps to attach the pad to the skin and make it ready for use with a medicament delivery device. For example, there is no need to remove a medicament delivery member protector such a as a needle sheath (as the medicament delivery member is protected within the pad). There is also no need to remove part of the pad to make it operational.

Figure 36:
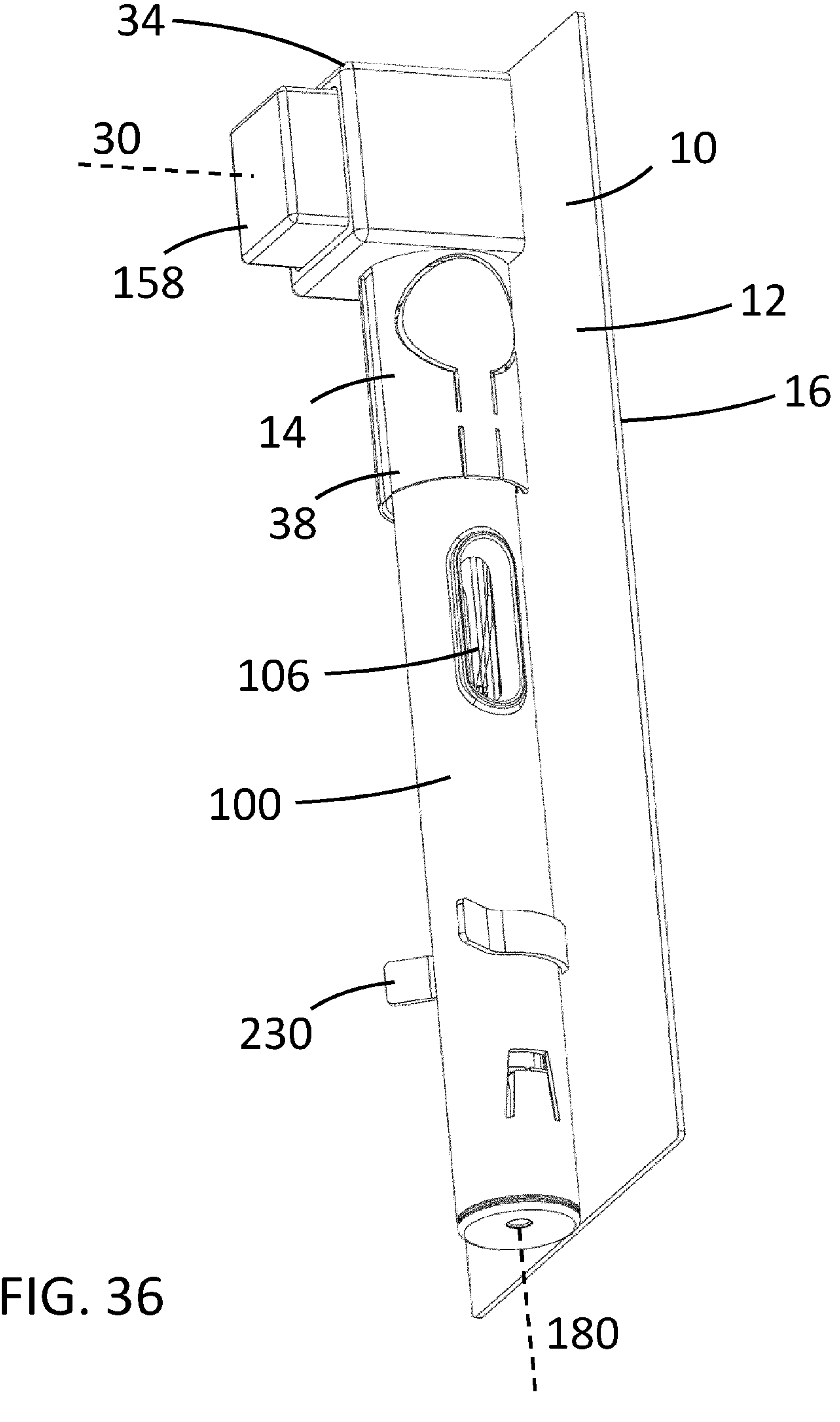
FIG. 36 shows a perspective view of another pad with an autoinjector.

Another alternative approach is shown from FIG. 36 onwards. The pad 10 comprises an attachment portion 14 configured to receive an autoinjector 100 (or more generally a medicament delivery device). The pad 10 also comprises a second attachment portion such as an adhesive portion 16 attached to the attachment portion 14, wherein the adhesive portion 16 is arranged at the proximal end 50 of the pad 10, and wherein the adhesive portion 16 is configured to attach the pad 10 to said injection site when the pad 10 is in use. An adhesive cover (not shown) could be provided. A housing 34 and a button 158 (in this case a first button housing 192) can also be seen.

Figure 37:
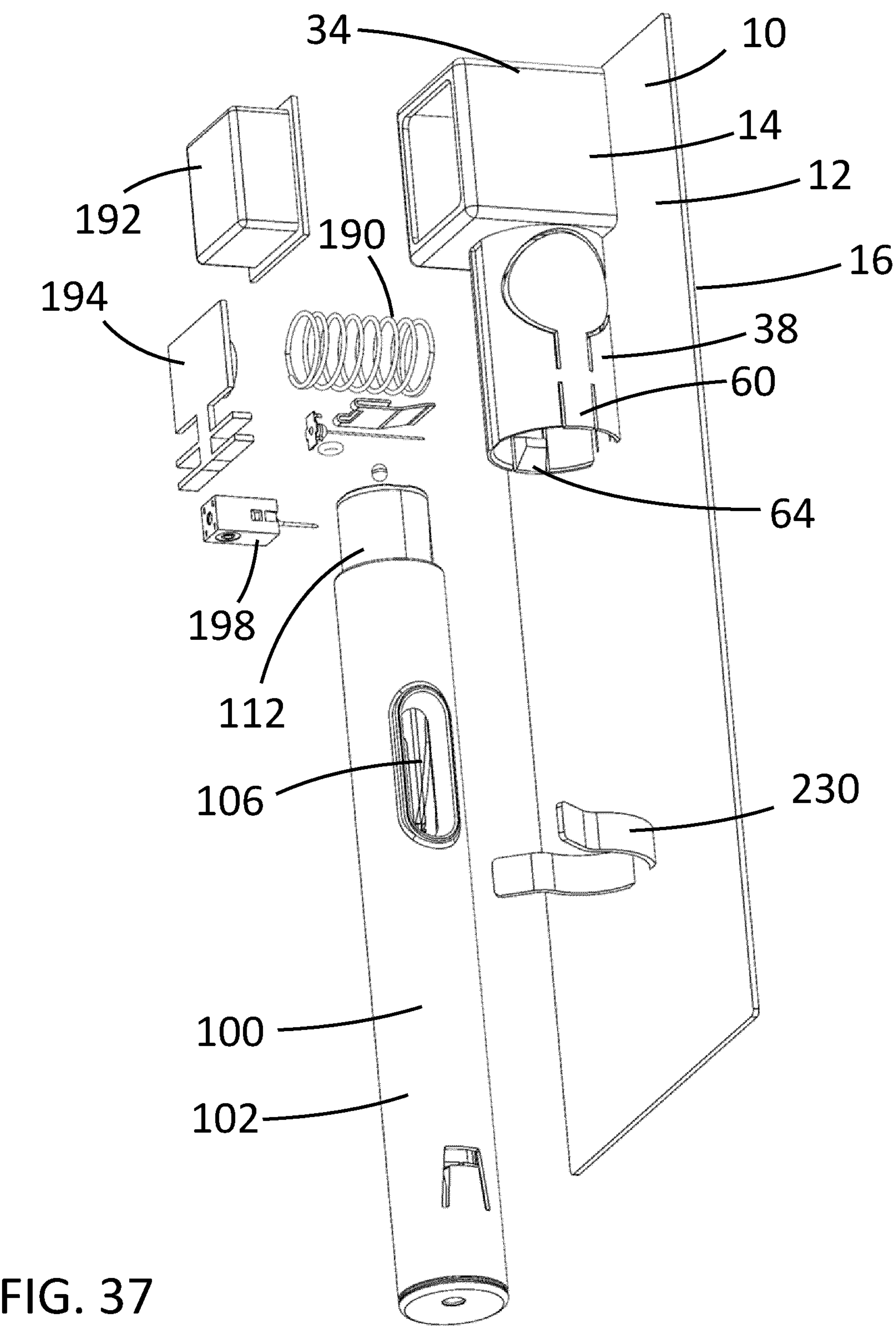
FIG. 37 shows a partially exploded view of the contents of FIG. 36.
Figure 38:
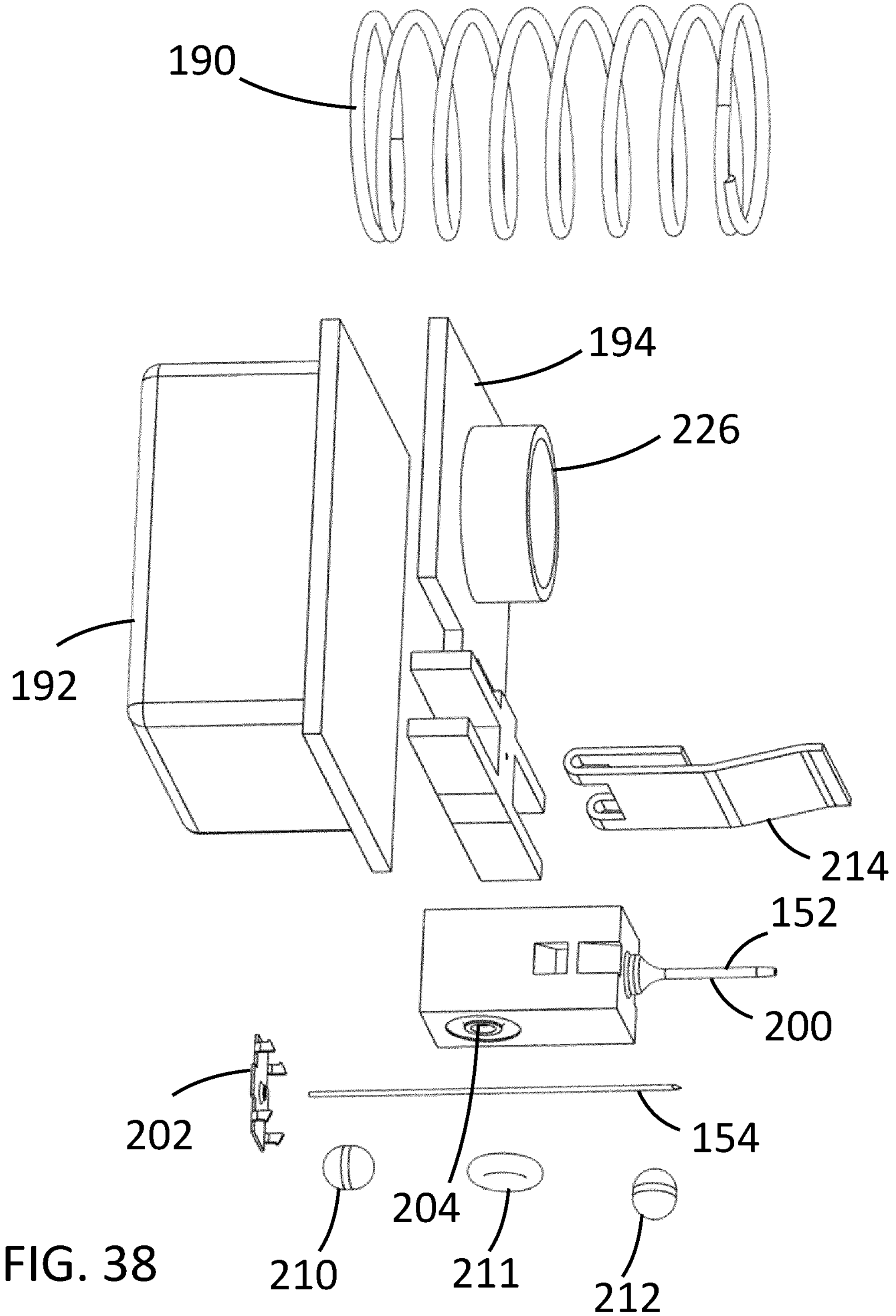
FIG. 38 shows an exploded perspective view of some of the components of the pad of FIG. 36.

The parts of the attachment portion inside the housing will now be described in more detail with reference to FIGS. 37 to 39. As can be seen in FIGS. 37 and 38, the pad comprises an optional spring 190, a button comprising a first button housing 192 and a second button housing 194, a cannula insertion needle 154 (which can be optional, for example in cases where the cannula is a rigid cannula), and a needle housing 198 comprising a first needle housing 200 and a second needle housing 202. The first needle housing 200 comprises a cannula 152. A number of other structural amendments could be made to the parts described—for example, the button and/or the needle housing could alternatively be a single integral part rather than two separate housings, and part or all of the needle housing could also be integrated as a single integral part with part or all of the button. Several other optional features are shown, including several seals 210, 211, 212 and a spacer 214.

Figure 39:
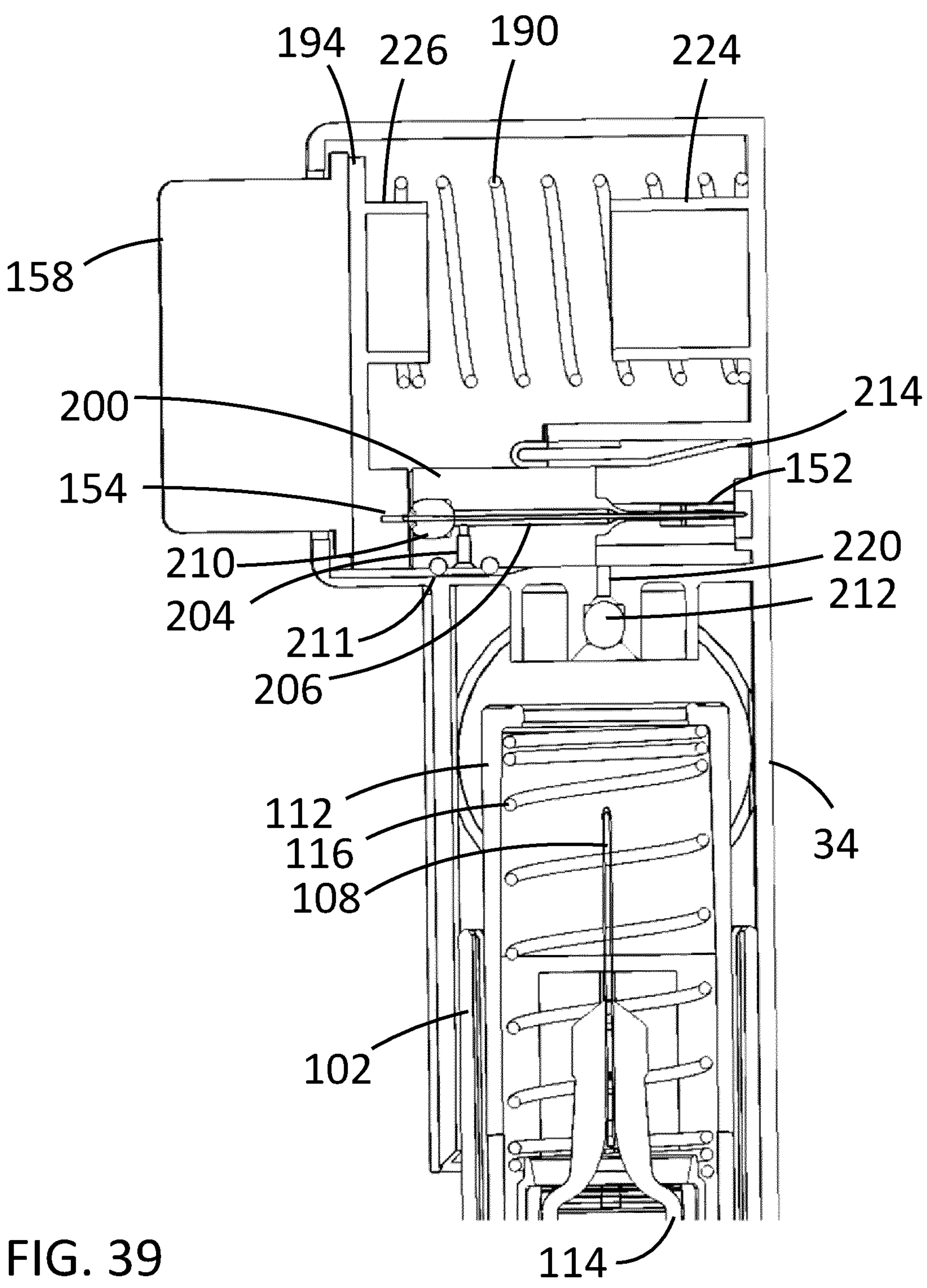
FIG. 39 shows a cross-section view of part of the contents of FIG. 36.

When assembled, the cannula insertion needle 154 is attached to the button (to the second button housing 194 in this particular example), and extends into the needle housing and into the cannula as can be seen in FIG. 39, for example. The cannula 152 and the cannula insertion needle 154 extend in the direction of the axis 30.

The optional housing seal 210 is held within the housing between the first needle housing 200 and the second needle housing 202, and can help stop medicament from leaking from the distal end of the needle housing 198 of the pad 10. The needle housing comprises a channel 204 (or tube); the channel extends perpendicular to the axis 30 in this example. The channel 204 is connected to a second channel 206 (or tube) of the needle housing, which fluidly connects the channel 204 to the cannula 152. As can be seen in FIG. 39 for example, the housing 34 comprises a channel 220 (or tube); when the button is depressed, the channel 204 and the channel 220 are aligned. The channel 220 may have a conical entrance at the end distal to the needle housing 198 to help align the needle of the autoinjector with the channel 204, although this entire structure is optional and the needle could simply interact directly with the channel 204. The housing interaction seal 211 can be provided to minimise or avoid leakage of medicament in the gap between the needle housing and the housing. The spacer 214 can help push the needle housing and the housing together, which can also help reduce or avoid leakage between the channel 220 and the channel 204. The spacer is arranged between the needle housing and a wall of the housing (or alternatively a rib or protrusion of the housing). In this example, the spacer is flexible and biased when in place, meaning that it can constantly push the needle housing towards the housing to help minimise leakage. More generally, the spacer could be a resilient member such as a spring. The channel seal 212 (which can have a pre-existing hole through it or can be pierced by the needle during use of the pad) is arranged in the housing and can help reduce or avoid leakage from the channel 220 of the housing 102.

The housing also houses an optional spring 190 (or alternatively another type of resilient member). The spring is arranged between the housing and the button. Optionally, the housing comprises a spring guide 224 and/or the button comprises a spring guide 226. The spring guide(s) can keep the spring in position within the housing. Another functionality that can be provided by the spring guide or spring guides is that they can restrict the travel of the button (which could control cannula insertion depth), although this is optional (and could alternatively be provided by another component, such as by the needle housing). Provision of the spring 190 can be beneficial as it can push the button back in the distal direction automatically after the button is released, thereby also pulling the cannula insertion needle back out of the injection site (and removing the need for the user to manually pull the button (and thereby the cannula insertion needle) back in the distal direction).

Figures 40, 41:
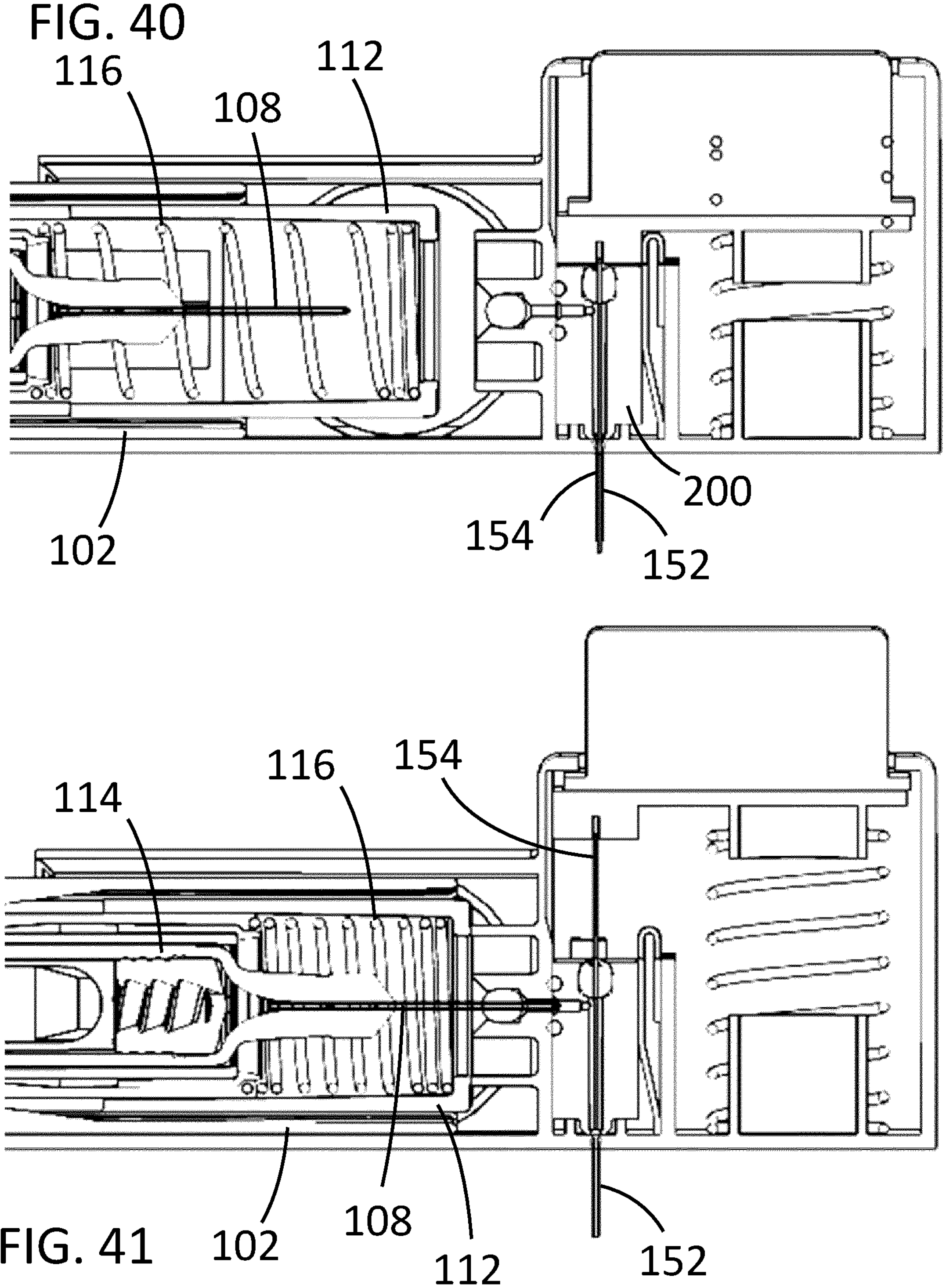
FIG. 40 shows a cross-section view as in FIG. 39, but after the button has been moved in the proximal direction.
FIG. 41 shows a cross-section view as in FIG. 39, but after the button has been moved back in the distal direction.

In this example, the method of operation is similar to the method described for other examples herein, for example with reference to FIGS. 30 to 33. First, the pad 10 is attached to an injection site. Second, the autoinjector (or medicament delivery device more generally) is attached to the pad (though the first and second steps could be reversed). Third, the button is pushed in the proximal direction, thereby inserting the cannula and the cannula insertion needle of the pad into the injection site (FIG. 40 shows the relative positions of the components at this point—although the position of the spring 190 has not been adjusted in FIG. 40) and the button is then released (or pulled in the distal direction) to remove the cannula insertion needle from the injection site (although the second and third steps could be reversed). Removing the cannula insertion needle from the injection site is not necessarily essential, but is generally preferable to help provide an open fluid path for the medicament. Finally, the autoinjector is activated to inject the medicament into the injection site via the pad (FIG. 41 shows the relative positions of the components at this point).

After injection of the medicament, the medicament delivery device can be removed from the pad, and the pad can be removed from the medicament delivery site. As mentioned above, the needle of the pad could optionally be retracted (i.e. moved in the distal direction back out of the injection site), for example by distal movement of the button of the pad. Optionally, the medicament delivery device can be removed from the pad but the pad kept on the injection site (typically with the needle of the pad still inserted in the injection site), and a second medicament delivery device can be inserted into the pad, allowing for a second injection (either a second dose of the same medicament or of a different medicament). In general, one or more subsequent injections could be carried out in this way, either immediately after the first injection or spaced apart in time.

Instead of an autoinjector as shown in FIG. 35, other autoinjectors or more generally other medicament delivery devices could be used, and the pad design could be altered to accommodate different shapes or types of autoinjector or medicament delivery device more generally. For example, the pad could be configured for use with a medicament delivery device such as the one shown in FIG. 28, with the pad comprising a medicament delivery device insertion needle configured to pierce a membrane of the medicament delivery device.

In the example shown in FIG. 35, the longitudinal axis 180 of the autoinjector 100 is perpendicular to the axis 30, although other angles are also possible. The extent of the flange 12 as shown in FIG. 36 could be varied, and more broadly speaking the flange is optional as in other examples described herein. Providing the flange can be beneficial, though, for example by increasing the available area for attaching the pad at the injection site and/or for supporting the autoinjector 100. Examples of optional support for the autoinjector include the tubular portion 38 (extending perpendicular to the axis 30 in this example, in contrast to the parallel example shown in FIG. 5) and the clip 230. The tubular portion 38 comprises an attachment arm 60 with a protrusion 64; this can engage a feature of the autoinjector (the window 106 in this example) to hold the autoinjector in place during medicament delivery. Alternatively or additionally, other attachment systems (and optionally subsequent detachments systems as well, depending on the design) could be used to hold the autoinjector on the pad of FIG. 35 (and optionally subsequently release the autoinjector from the pad), such as the approaches shown in FIGS. 1 to 19. Seals such as the housing interaction seal 211 can be a separate part or an integral part of the needle housing or the housing. The housing interaction seal can also help hold the needle housing in place during injection, for example by provision of recesses on both the housing and the needle housing in which the housing seal sits, thereby increasing the friction required to push the needle housing relative to the housing during injection. Alternatively or additionally, snap fits can help hold the needle housing in place relative to the housing during injection. Optionally, to stop a user from inserting the cannula insertion needle 154 multiple times, a lock could be provided that is engaged once the cannula is inserted. For example, this lock could be a biased arm in the housing that springs out into the gap between the button and the needle housing when the button moves back in the distal direction.

Figure 42:
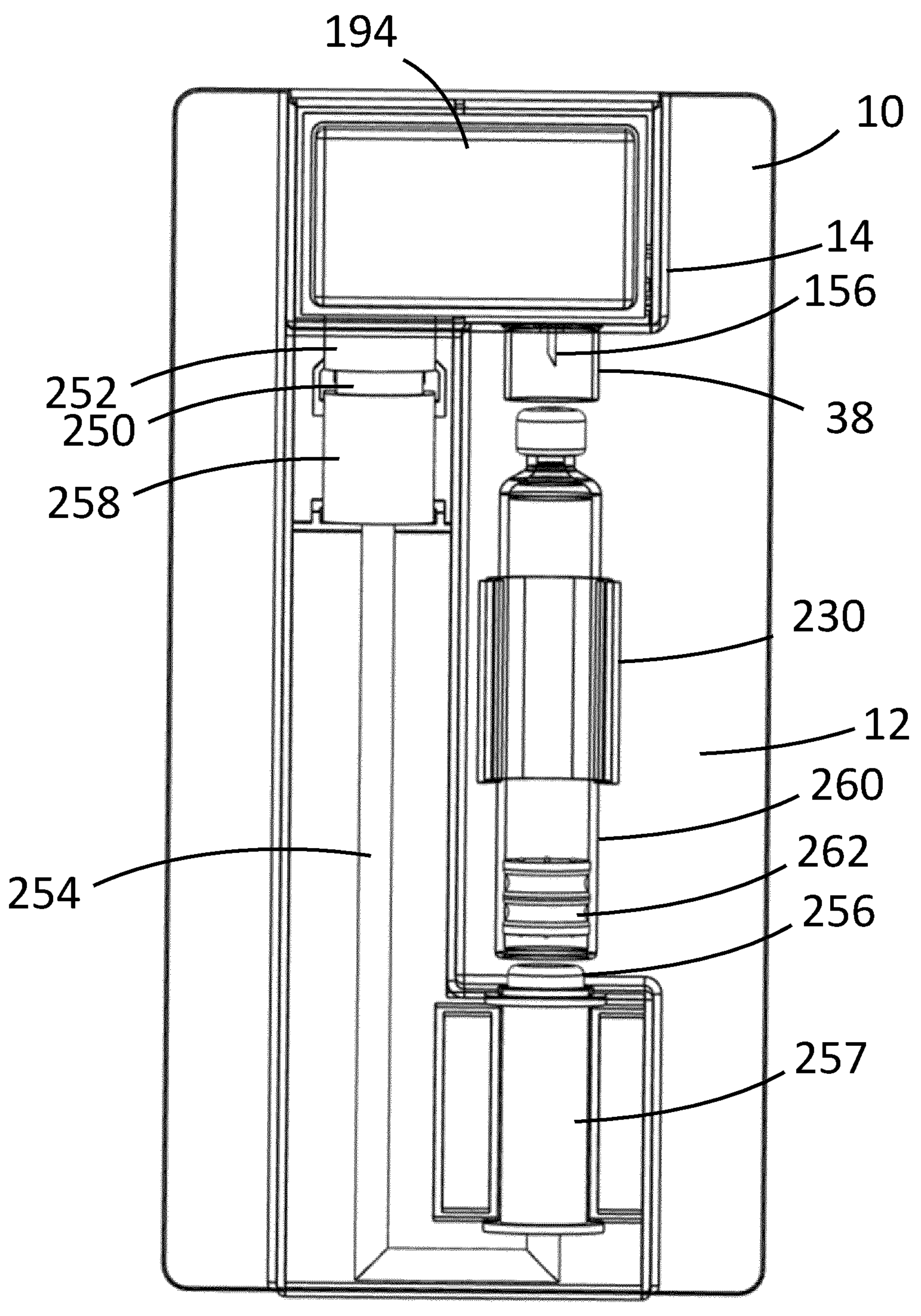
FIG. 42 shows a partially transparent view of another example pad with a cartridge, looking in the proximal direction.

FIG. 42 shows another example. Much of the structure in this example is the same as that shown in the example described above with reference to FIGS. 36 to 41, and a full explanation of the depicted structure and the various alternatives will therefore not be repeated.

Figure 32:
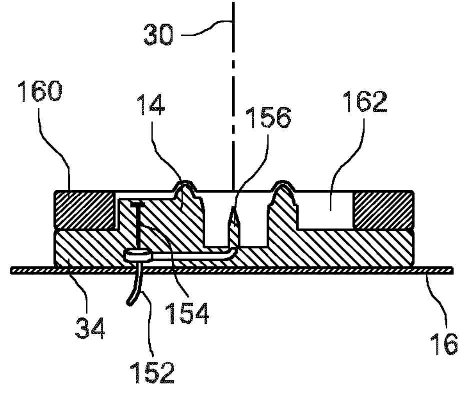
FIG. 32 shows a cross-sectional side view of the pad of FIG. 30.

The main functional difference between the example shown in FIG. 42 and the example shown in FIG. 35 is that the pad shown in FIG. 42 is configured to receive a medicament container (in this case a cartridge) rather than an autoinjector—that is, instead of the needle being in the medicament delivery device, it is attached to the pad—this is similar to the approach of the example in FIG. 32, for example. In another alternative, the needle is provided separately and added to the cartridge or to the pad before injection.

FIG. 42 shows a pad 10 and a cartridge 260. The pad 10 comprises a flange 12, an attachment portion 14 and a second attachment portion (not shown). Various parts of the attachment portion 14 can be seen, including a tubular portion 38, a medicament delivery device insertion needle 156, a second button housing 194, a clip 230, a gas cartridge (gas canister) 250, a first gas cartridge housing 252, a gas pipe 254, a plunger rod 256, a plunger rod housing 257 and a second gas cartridge housing 258. The cartridge 260 comprises a stopper 262.

Figure 43:
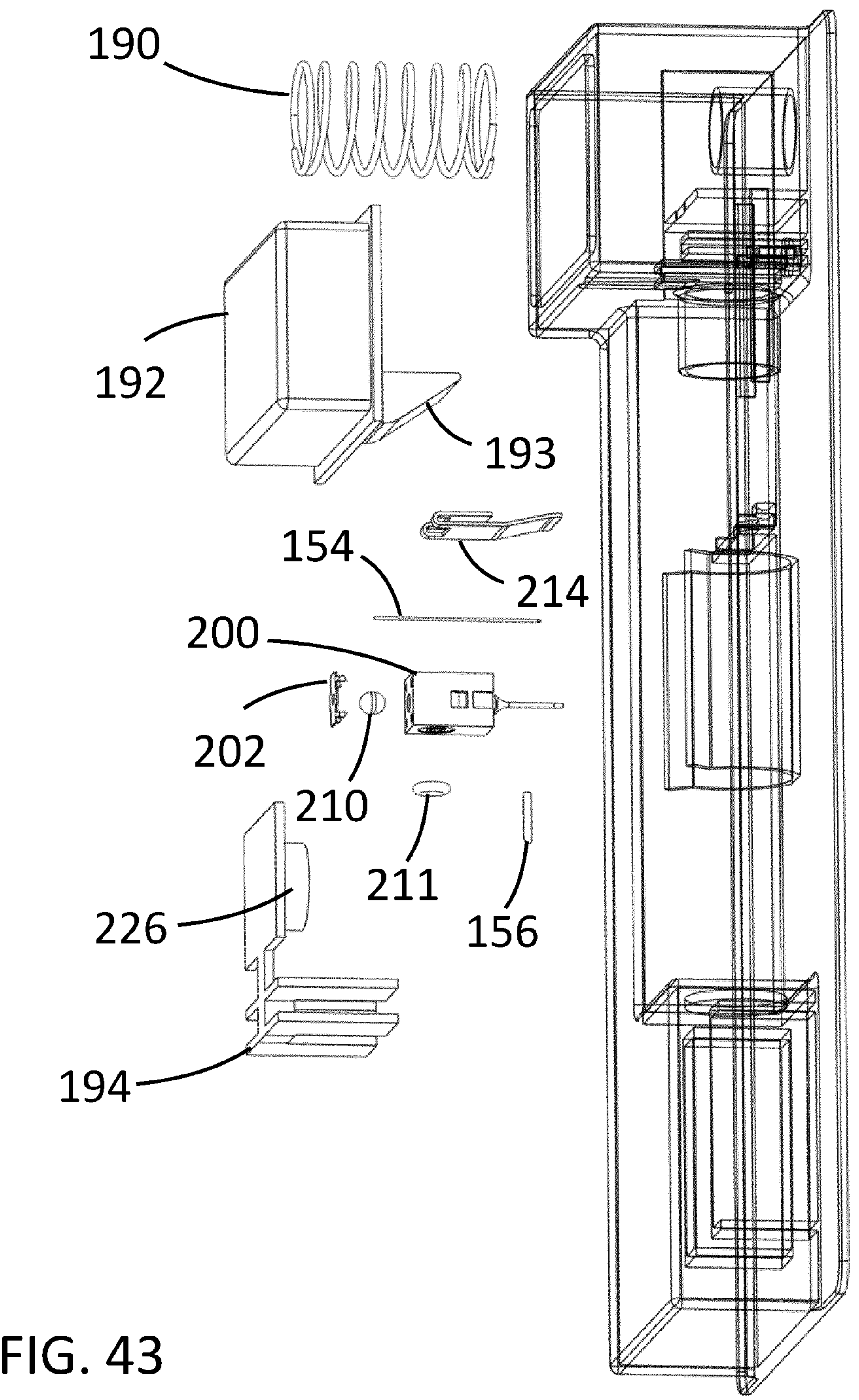

FIG. 43 shows further features of the attachment portion 14 of the pad, namely a cannula insertion needle 154, a medicament delivery device insertion needle 156, a spring 190, a first button housing 192, a second button housing 194, a first needle housing 200, a second needle housing 202, a housing seal 210, and a housing interaction seal 211. The medicament delivery device insertion needle 156 is attached to the housing 34. The button (in this example specifically the first button housing 192) comprises an optional wedge 193 that is able to activate the gas cartridge when the button is pressed. Alternatively, the gas cartridge could be activated in another way, for example by a separate button or directly upon insertion of the gas cartridge.

Figures 44, 45:
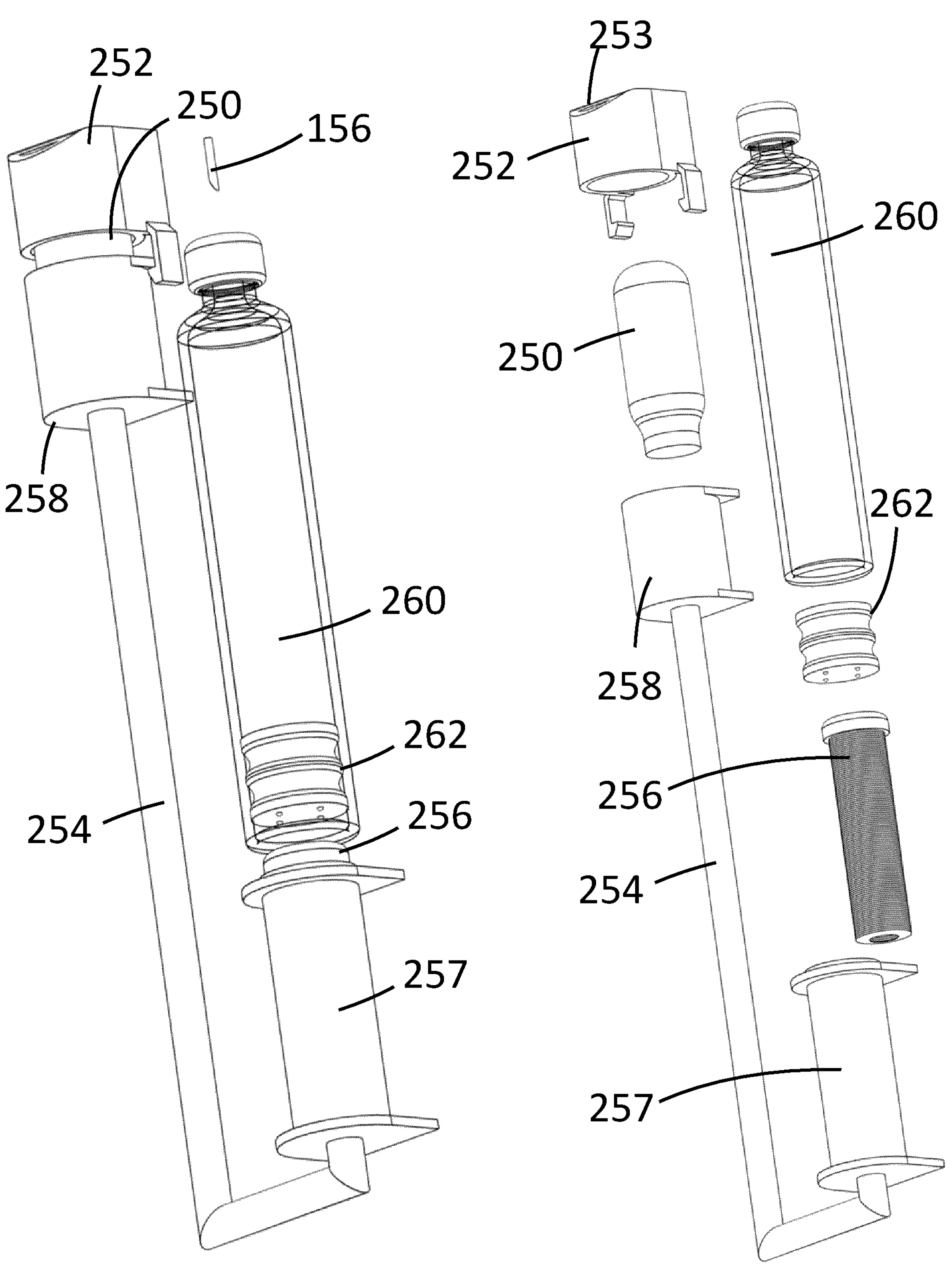
FIG. 44 shows a perspective view of some of the components of the pad of FIG. 42 along with a cartridge.
FIG. 45 shows an exploded view of most of the components of FIG. 44.

FIGS. 44 and 45 primarily show the components of the pad that are provided to push the stopper of the cartridge to expel the medicament from the cartridge (although in other examples this could alternatively just be done manually, like with a syringe), along with the medicament delivery device insertion needle 156 for context. In this case, these components are not all aligned along the same axis—this particular arrangement can be beneficial in terms of space utilisation, but these components could alternatively all be aligned along the same axis.

FIGS. 44 and 45 show a cartridge 260 (shown as see-through) with a stopper, along with components of the pad, namely a gas cartridge 250, a first gas cartridge housing 252, a gas pipe 254, a plunger rod 256, a plunger rod housing 257 and a second gas cartridge housing 258. The gas pipe 254, the plunger rod housing 257 and the second gas cartridge housing 258 are attached together (optionally as a single integral part). The gas cartridge 250 is arranged between the first gas cartridge housing 252 and the plunger rod 256. The first gas cartridge housing 252 is moveable relative to the second gas cartridge housing 258, and can be pushed via an angled surface 253 towards the second gas cartridge housing 258 to activate the gas cartridge 250. The plunger rod 256 is housed inside the plunger rod housing 257. The cartridge 260 is arranged adjacent to and coaxially with the plunger rod 256. The gas cartridge contains a pressurised fluid; typically a pressurised gas. The gas cartridge could be replaceable to allow the same pad to be used multiple times.

A method of use will now be described, focussing on the components shown in FIG. 44. To use the pad, a cartridge is first inserted into the pad and the pad then attached to the injection site (or vice versa). The button is then pressed, moving it in the proximal direction, which inserts the cannula 152 and the cannula insertion needle 154 into the injection site and activates the gas cartridge 250 (subsequent movement of the button in the distal direction removes the cannula insertion needle 154 from the injection site if desired). Once the gas cartridge 250 is activated, gas will flow from the cartridge through the gas pipe and impact the plunger rod, pushing the plunger rod against the stopper and thereby pushing the cartridge against the medicament delivery device insertion needle 156 (if the cartridge is not already attached to the medicament delivery device insertion needle 156). The plunger rod then continues to push the stopper, pushing the stopper towards the medicament delivery device insertion needle 156 and thereby pushing the medicament out of the cartridge, through the channels 204, 206 and the cannula 152 into the injection site.

Further alternatives will now be described, which could be used for both the designs in FIGS. 42 to 45 and more generally. Optionally, a membrane is placed around the medicament delivery device insertion needle 156; this can help maintain sterility. The membrane can be pierced by the medicament delivery device insertion needle 156 when the medicament delivery device insertion needle 156 pierces the cartridge. Optionally, the plunger rod is a hollow tubular concertina and is attached to the gas pipe 254 or the plunger rod housing 257 at the end of the plunger rod distal from the end of the plunger rod that interacts with the stopper during use. In this example, the plunger rod expands in length when the gas pipe 254 is pressurised during use. This approach can be preferable compared to other alternatives, for example the alternative option of using a cylindrical plunger rod, as it can reduce the pressure left in the used device, can make it easier to reset the device in the example of a reuseable system, and/or can make the used device safer as there is no danger of the plunger rod coming out entirely if a user removes the canister after use.

Many of the examples described herein could be used with a fully functioning medicament delivery device such as a fully functioning autoinjector. That is, the medicament delivery device (for example an autoinjector) with which the pad is used can be a fully functioning device in its own right.

Optionally, some of the components (or parts of some of the components) of the pads described herein could be transparent. This can allow medicament delivery device users to see the medicament delivery device (in particular the proximal end of the medicament delivery device) during medicament delivery device use. This can be useful in particular to allow users to see whether the medicament delivery device is functioning as expected (for example whether the medicament delivery member guard has retracted correctly). For example, part or all of the attachment portion of the pad could be transparent (in a particular example, part or all of the tubular portion 38 could be transparent). In a similar vein, an opening such as a slot or a cut-out could additionally or alternatively be provided in the attachment portion (for example in the tubular portion 38). Provision of an opening can allow users to see whether the medicament delivery device is functioning as expected (for example whether the medicament delivery member guard has retracted correctly).

Although various modifications are already described, various further modifications to the embodiments described are also possible and will occur to those skilled in the art without departing from the present disclosure which is defined by the following claims.

Some aspects of the present disclosure are described in the following clauses.

1. A pad (10) extending along an axis (30) from a proximal end to a distal end, where the proximal end is the end of the pad adjacent to an injection site when the pad is in use, the pad comprising an attachment portion (14) configured to receive a medicament delivery device (100, 150) and a second attachment portion (16) attached to the attachment portion, wherein the second attachment portion is arranged at the proximal end of the pad, and wherein the second attachment portion is configured to attach the pad to said injection site when the pad is in use.

2. The pad of clause 1, wherein the second attachment portion is an adhesive portion, and the adhesive portion is configured to adhere the pad to said injection site when the pad is in use.

3. The pad of clause 1 or 2, wherein the attachment portion is at the distal end of the pad.

4. The pad of clause 2 or 3, wherein the adhesive portion of the pad comprises a flange, and wherein the flange extends further from the axis in a radial direction than the attachment portion.

5. The pad of clause 4, wherein the flange is flexible.

6. The pad of any of clauses 2 to 5 wherein the adhesive portion comprises an adhesive layer.

7. The pad of any of clauses 1 to 6, where the attachment portion comprises a tubular portion.

8. The pad of any of clauses 1 to 7, wherein the pad comprises a medicament delivery member.

9. The pad of clause 8, wherein the medicament delivery member is a cannula.

10. The pad of clause 8 or 9, wherein the pad comprises an insertion mechanism configured to insert the medicament delivery member into the injection site.

11. The pad of any of clauses 8 to 10, wherein the insertion mechanism comprises a needle for inserting the medicament delivery member into the injection site.

12. The pad of any of clauses 8 to 11, wherein the needle of the insertion mechanism is offset from the axis.

13. The pad of any of clauses 8 to 11, wherein the attachment portion and the needle of the insertion mechanism are spaced apart in a radial direction relative to the axis.

14. The pad of any of clauses 8 to 13, comprising an insertion needle configured to pierce a medicament delivery container of a medicament delivery device.

15. The pad of clause 14, wherein the insertion needle is spaced apart from the needle for inserting the medicament delivery member into the injection site.

16. The pad of clause 14 or 15, comprising a tube or channel extending between the insertion needle and the medicament delivery member.

17. The pad of any of clauses 1 to 16, wherein the attachment portion is configured to releasably receive the medicament delivery device.

18. The pad of clause 17, wherein the attachment portion comprises a friction lock.

19. The pad of clause 17 or 18, wherein the attachment portion comprises a release mechanism which, upon being actuated, releases the medicament delivery device from the pad.

20. The pad of any of clauses 1 to 19, wherein the attachment portion comprises a slider.

21. The pad of clause 20, wherein the slider comprises a first arm and a second arm, wherein the first arm and the second arm are spaced apart from one another and configured to grip a medicament delivery device between the first arm and the second arm.

22. The pad of clause 21, wherein the first arm has a first end and a second end and the second arm has a first end and a second end, wherein the first end of the first arm is attached to the first end of the second arm, and wherein the second end of the first arm and the second end of the second arm are spaced apart from one another.

23. The pad of clause 21 or 22, wherein the first arm and the second arm are flexible so that the second ends of the first arm and the second arm can move relative to one another.

24. The pad of any of clauses 21 to 23, wherein the first arm and the second arm are configured to form a locking position and a release position.

25. The pad of clause 24, wherein the locking position and the release position each describe an opening between the arms, and wherein the distance between the arms of the opening of the release position is larger than the distance between the arms of the opening of the locking position.

26. The pad of any of clauses 20 to 25, wherein the attachment portion comprises a housing, and the slider is arranged inside the housing.

27. The pad of any of clauses 1 to 19, wherein the attachment portion comprises a user manipulation portion and a medicament delivery device engagement portion, wherein the attachment portion is configured such that when a user manipulates the user manipulation portion, the medicament delivery device engagement portion can be disengaged from said medicament delivery device.

28. The pad of clause 27, wherein the user manipulation portion comprises a flexible section extending around the axis, wherein the attachment portion is configured such that when the user changes the shape of the flexible section, at least a portion of the medicament delivery device engagement portion is moved further from the axis.

29. The pad of clause 28, wherein the flexible section is a flexible elliptical section, and wherein the attachment portion is configured such that changing the shape of the flexible section reduces the ellipticalness of the flexible elliptical section.

30. The pad of any of clauses 27 to 29, wherein the user manipulation portion is attached to the medicament delivery device engagement portion by one or more arms.

31. The pad of any of clauses 27 to 30, wherein the medicament delivery device engagement portion comprises a groove or a protrusion configured to engage with a corresponding protrusion or groove on said medicament delivery device.

32. The pad of any of clauses 1 to 20, wherein the attachment portion comprises an arm configured to engage a feature of a medicament delivery device.

33. The pad of clause 32, wherein the arm is configured to engage with a window frame of said medicament delivery device.

34. The pad of any of clauses 32 or 33, wherein the arm comprises a protrusion extending perpendicular to the axis.

35. The pad of clause 34, wherein the protrusion is configured to engage with a window frame of said medicament delivery device.

36. The pad of any of clauses 1 to 19, wherein the attachment portion comprises a handle and an engagement portion attached to the handle, wherein the engagement portion is configured to releasably attach to an attachment portion of said medicament delivery device such that the engagement portion is released from the medicament delivery device when the handle is pushed towards the axis.

37. The pad of clause 36, wherein the engagement portion is between the axis and the handle.

38. The pad of any of clauses 1 to 19, wherein the attachment portion comprises a first handle, a second handle, a first engagement portion and a second engagement portion, wherein the first engagement portion and the second engagement portion are each configured to releasably engage with an attachment portion of said medicament delivery device, wherein the first handle is attached to the first engagement portion and the second handle is attached to the second engagement portion, and wherein pushing the first handle towards the second handle releases the engagement portions from the attachment portion of said medicament delivery device.

39. The pad of clause 38, wherein the first engagement portion is between the axis and the first handle, and wherein the second engagement portion is between the axis and the second handle.

40. The pad of any of clauses 36 to 39, wherein pushing the handle or handles towards the axis moves at least a part of the engagement portion or at least part of the first and/or second engagement portion in the circumferential direction relative to the axis.

41. The pad of any previous clause, wherein the attachment portion is configured to receive a medicament delivery device with a longitudinal axis of the medicament delivery device extending perpendicular to the axis (30).

42. The pad of any previous clause, wherein the attachment portion comprises a tubular portion, and wherein a longitudinal axis of the tubular portion extends perpendicular to the axis (30).

43. The pad of any previous clause, wherein the pad comprises a medicament delivery member and the attachment portion comprises a button, and wherein pressing the button moves the medicament delivery member in the proximal direction.

44. The pad of clause 43, wherein the pad comprises a resilient member and a housing, and the resilient member extends between the housing and the button.

45. The pad of clause 43 or 44, wherein the pad comprises a housing, wherein the pad comprises a medicament delivery member housing comprising a cannula, and wherein the medicament delivery member housing is arranged in the housing.

46. The pad of clauses 45, wherein the medicament delivery member housing comprises a channel and the channel is not aligned with the attachment portion before the button is pressed and the channel is aligned with the attachment portion after the button is pressed.

47. The pad of any of clauses 43 to 46, wherein the pad is arranged so that a medicament delivery can only occur after the button has been pressed.

48. The pad of any previous clause, wherein the pad comprises a gas canister and a plunger rod configured to engage a cartridge, wherein activation of the gas canister results in the plunger rod causing expulsion of a medicament from said cartridge.

49. A medicament delivery member guard comprising the pad of any of clauses 1 to 48.

50. A medicament delivery device comprising the medicament delivery member guard of clause 49.

51. Apparatus comprising the pad of any of clauses 1 to 40 and a medicament delivery device.

52. Apparatus according to clause 51, wherein the medicament delivery device comprises a guard.

53. Apparatus according to clause 52, wherein the guard is a medicament delivery member guard or a membrane guard.

54. Apparatus according to any of clauses 51 to 53, wherein the medicament delivery device comprises a protrusion or recess configured to engage with the attachment portion of the pad.

55. Apparatus according to clause 54, wherein the medicament delivery device comprises a housing, and wherein the protrusion or recess is on the housing.

56. Apparatus according to any of clauses 51 to 55, wherein the medicament delivery device comprises a window frame, and the attachment portion of the pad is configured to engage the window frame.

57. The subject matter of any of clauses 1 to 56, wherein the medicament delivery device is an autoinjector.

58. The subject matter of any of clauses 1 to 57, wherein the medicament delivery device comprises a medicament container.

59. The subject matter of any of clauses 1 to 57, wherein the medicament delivery device comprises a medicament delivery member.

60. An autoinjector comprising a housing, wherein the housing comprises an attachment portion, wherein the attachment portion is configured to engage with a corresponding attachment portion on a pad according to one of clauses 1 to 40.

61. A method of carrying out an injection, the method comprising the steps of attaching a pad to an injection site attaching an autoinjector to the pad removing the autoinjector from the injection site.

62. The method of clause 61, wherein the method additionally comprises the step of removing the pad from the injection site.

63. The method of clause 62, wherein the injection automatically starts when the autoinjector is attached to the pad.

64. The method of any of clauses 61 to 63, wherein the autoinjector and the pad are removed together from the injection site.

65. The method of any of clauses 61 to 63, wherein the autoinjector is removed from the pad, and the pad is subsequently removed from the injection site.

66. A method of carrying out an injection, the method comprising the steps of attaching a pad to a dose delivery site, attaching a medicament delivery device to the pad, injecting a medicament into the dose delivery site, and removing the medicament delivery device.

67. The method of clause 66, wherein the step of attaching a pad to a dose delivery site consists of attaching the pad and inserting a medicament delivery member into the dose delivery site.

68. The method of any of clauses 61 to 66, wherein the pad is a pad according to any of clauses 1 to 40.

69. A pad configured to attach a medicament delivery device to a medicament delivery site to carry out an injection, the pad comprising an adhesive for attaching the pad at the medicament delivery site and an attachment portion configured to hold a medicament delivery device at the medicament delivery site.

70. The pad of clause 69, wherein the medicament delivery device is an autoinjector or a medicament cartridge.

71. The pad of clause 69, wherein the pad is configured to hold the medicament delivery device at the medicament delivery site for the duration of an injection.

72. The pad of clause 69, wherein the pad is configured to support the medicament delivery device so that the injection can proceed in a hands-free manner once the injection has started.

73. A pad for attaching an autoinjector to a user, the pad comprising an adhesive portion for attachment to a medicament delivery site and a housing attached to the adhesive portion, the housing comprising an attachment portion, and wherein the attachment portion is for attaching an autoinjector to the pad.

74. The pad of clause 73, wherein the pad is attached to the autoinjector such that the autoinjector can be used in a hands-free manner.

75. A method of hands-free injection of a medicament, the method comprising attaching a pad to a dose delivery site, attaching a medicament delivery device to the pad, injecting a medicament into the dose delivery site while the medicament delivery device is attached to the pad, and removing the medicament delivery device.

The invention claimed is:

1. A pad comprising:

a distal end;

a proximal end configured to be placed adjacent to an injection site when the pad is in use;

an axis extending from the proximal end to the distal end;

a first attachment portion configured to receive a medicament delivery device; and a second attachment portion attached to the first attachment portion, wherein the second attachment portion is arranged at the proximal end of the pad, wherein the second attachment portion is configured to attach the pad to said injection site when the pad is in use, and wherein the first attachment portion comprises a slider, the slider comprising a first slider arm and a second slider arm, wherein the first slider arm and the second slider arm are spaced apart from one another and configured to grip the medicament delivery device between the first slider arm and the second slider arm.

2. The pad of claim 1, wherein the second attachment portion is an adhesive portion, and the adhesive portion is configured to adhere the pad to said injection site when the pad is in use.

3. The pad of claim 1, wherein the pad comprises a medicament delivery member.

4. The pad of claim 3, wherein the medicament delivery member is a cannula.

5. The pad of claim 3, wherein the pad comprises an insertion mechanism.

6. The pad of claim 5, wherein the insertion mechanism comprises a needle for inserting the medicament delivery member into the injection site.

7. The pad of claim 6, wherein the needle of the insertion mechanism is offset from the axis.

8. The pad of claim 1, wherein the first attachment portion is configured to releasably receive the medicament delivery device.

9. The pad of claim 1, wherein the first attachment portion comprises a user manipulation portion and a medicament delivery device engagement portion, wherein the first attachment portion is configured such that when a user manipulates the user manipulation portion, the medicament delivery device engagement portion can be disengaged from said medicament delivery device.

10. The pad of claim 1, wherein the first attachment portion comprises an attachment arm configured to engage a feature of the medicament delivery device.

11. The pad of claim 10, wherein the feature of said medicament delivery device is a window frame.

12. The pad of claim 1, wherein a longitudinal axis of the medicament delivery device extends perpendicular to the axis extending from the proximal end to the distal end.

13. An assembly comprising an autoinjector and the pad according to claim 1.

14. A pad for use with a medicament delivery device, the pad comprising:

a proximal end and a distal end, where the proximal end has a through opening;

an axis that extends from the proximal end to the distal end;

a first attachment portion configured to releasably receive a portion of the medicament delivery device such that a proximal end portion of the medicament delivery device aligns with the through opening; and a second attachment portion arranged at the proximal end of the pad comprising an adhesive positioned adjacent the through opening, where contacting the adhesive to a delivery site will fix the pad to the delivery site and will support the medicament delivery device when inserted into the first attachment portion, wherein the through opening is sized to allow a medicament delivery member to pass through and exit the through opening and be inserted into the delivery site, and wherein the first attachment portion comprises a slider having a first arm and a second arm, where the first arm and the second arm are spaced apart from one another and where movement of the first arm and the second arm relative to a base portion of the pad will grip the medicament delivery device between the first arm and the second arm.

15. The pad of claim 14, wherein the first attachment portion comprises a flexible user manipulation portion and a medicament delivery device engagement portion, wherein when a user flexes and manipulates the user manipulation portion, the medicament delivery device engagement portion will disengage from the medicament delivery device that is aligned with the through opening.

* * * * *